United States Patent
Akdogan et al.

(10) Patent No.: US 9,358,499 B2
(45) Date of Patent: *Jun. 7, 2016

(54) MODULAR DISPENSING DEVICES FOR INFORMING A USER OF A NUMERIC AMOUNT OF CONSUMABLES AND A SCHEDULE FOR DISPENSING THE CONSUMABLES

(71) Applicant: Makefield LLC, Newtown, PA (US)

(72) Inventors: Kutadgu Akdogan, New York, NY (US); Kalyan C. Vepuri, Newtown, PA (US); Christian Von Heifner, Brooklyn, NY (US)

(73) Assignee: Makefield LLC, Newtown, PA (US)

( * ) Notice: Subject to any disclaimer, the term of this patent is extended or adjusted under 35 U.S.C. 154(b) by 285 days.

This patent is subject to a terminal disclaimer.

(21) Appl. No.: 14/214,797

(22) Filed: Mar. 15, 2014

(65) Prior Publication Data

US 2014/0263425 A1  Sep. 18, 2014

Related U.S. Application Data

(60) Provisional application No. 61/800,973, filed on Mar. 15, 2013.

(51) Int. Cl.
  *G08B 21/00* (2006.01)
  *B01D 53/26* (2006.01)
  (Continued)

(52) U.S. Cl.
  CPC ............. *B01D 53/261* (2013.01); *A61J 7/0076* (2013.01); *A61J 7/02* (2013.01); *A61J 7/0481* (2013.01); *G07C 9/00134* (2013.01); *G07F 9/026* (2013.01); *G07F 11/44* (2013.01);
  (Continued)

(58) Field of Classification Search
  CPC ......... A61J 1/03; A61J 7/0076; A61J 7/0481; G06F 19/3462
  USPC ...................................................... 340/309.7
  See application file for complete search history.

(56) References Cited

U.S. PATENT DOCUMENTS

| 4,695,954 A | 9/1987 | Rose et al. |
| 5,240,139 A | 8/1993 | Chirnomas |

(Continued)

FOREIGN PATENT DOCUMENTS

| WO | WO-2011054000 | 5/2011 |
| WO | WO2014145218 | 9/2014 |
| WO | WO-2016022714 | 2/2016 |

OTHER PUBLICATIONS

WIPO, "International Application Serial No. PCT/US14/029940, Preliminary Report on Patentability mailed Sep. 24, 2015", 14 pages.

(Continued)

*Primary Examiner* — Mark Rushing
(74) *Attorney, Agent, or Firm* — Strategic Patents, P.C.

(57) ABSTRACT

A dispensing device is improved through the inclusion of modular components, for example, mechanical interfaces to couple to a container and a base. The modular dispensing device may also include communication systems related to the container and the base. Specifically, the modular dispensing device may receive information such as the contents of the container (e.g., quantity, identity, etc.) and a schedule for dispensing the contents. Using this information, the modular dispensing device may control the dispensing of the contents of the container.

19 Claims, 19 Drawing Sheets

(51) Int. Cl.
*A61J 7/02* (2006.01)
*G07F 11/44* (2006.01)
*A61J 7/00* (2006.01)
*G07C 9/00* (2006.01)
*H04N 7/18* (2006.01)
*A61J 7/04* (2006.01)
*G07F 9/02* (2006.01)
*A61J 1/03* (2006.01)
*G06F 19/00* (2011.01)
*B01D 53/04* (2006.01)

(52) U.S. Cl.
CPC  *H04N 7/188* (2013.01); *A61J 1/03* (2013.01); *B01D 53/0454* (2013.01); *G06F 19/3462* (2013.01)

(56) References Cited

U.S. PATENT DOCUMENTS

| | | |
|---|---|---|
| 5,559,503 A | 9/1996 | Blahut |
| 5,597,995 A | 1/1997 | Williams et al. |
| 6,004,020 A | 12/1999 | Bartur |
| 6,253,955 B1 | 7/2001 | Bower et al. |
| 6,371,297 B1 | 4/2002 | Cha |
| 6,411,567 B1 | 6/2002 | Niemiec et al. |
| 6,471,087 B1 | 10/2002 | Shusterman |
| 6,507,275 B2 | 1/2003 | Romano et al. |
| 6,529,801 B1 | 3/2003 | Rosenblum |
| 6,604,019 B2 | 8/2003 | Ahlin et al. |
| 6,662,081 B1 | 12/2003 | Jacober et al. |
| 6,685,678 B2 | 2/2004 | Evans et al. |
| 6,892,941 B2 | 5/2005 | Rosenblum |
| 7,006,894 B2 | 2/2006 | de la Huerga |
| 7,080,755 B2 | 7/2006 | Laliberte et al. |
| 7,155,306 B2 | 12/2006 | Haitin et al. |
| 7,170,823 B2 | 1/2007 | Fabricius et al. |
| 7,253,411 B2 | 8/2007 | Kaushal et al. |
| 7,382,263 B2 | 6/2008 | Danowski et al. |
| 7,395,214 B2 | 7/2008 | Shillingburg |
| 7,471,993 B2 | 12/2008 | Rosenblum |
| 7,715,277 B2 | 5/2010 | de la Huerga |
| 7,755,478 B2 | 7/2010 | Niemiec et al. |
| 7,774,097 B2 | 8/2010 | Rosenblum |
| 7,844,361 B2 | 11/2010 | Jean-Pierre |
| 7,944,342 B2 | 5/2011 | Sekura |
| 7,978,564 B2 | 7/2011 | De La Huerga |
| 8,014,232 B2 | 9/2011 | Niemiec et al. |
| 8,019,471 B2 | 9/2011 | Bogash et al. |
| 8,116,907 B2 | 2/2012 | Hyde et al. |
| 8,212,677 B2 | 7/2012 | Ferguson |
| 8,391,104 B2 | 3/2013 | de la Huerga |
| 8,670,865 B2 | 3/2014 | Coe |
| 8,887,603 B2 | 11/2014 | Mitani et al. |
| 9,043,015 B2 | 5/2015 | Ratnakar |
| 9,218,458 B2 | 12/2015 | Baarman et al. |
| 2001/0002448 A1 | 5/2001 | Wilson et al. |
| 2002/0032582 A1 | 3/2002 | Feeney, Jr. et al. |
| 2003/0099158 A1* | 5/2003 | De la Huerga ........ A61J 1/1437 368/10 |
| 2004/0054436 A1 | 3/2004 | Haitin et al. |
| 2007/0088461 A1 | 4/2007 | Haitin et al. |
| 2007/0156282 A1 | 7/2007 | Dunn et al. |
| 2008/0093371 A1 | 4/2008 | Ubidia et al. |
| 2008/0300719 A1 | 12/2008 | Duke |
| 2009/0069742 A1 | 3/2009 | Larsen |
| 2009/0108016 A1 | 4/2009 | Brown et al. |
| 2009/0134181 A1 | 5/2009 | Wachman et al. |
| 2009/0167531 A1 | 7/2009 | Ferguson |
| 2009/0182582 A1 | 7/2009 | Hammon |
| 2009/0192648 A1 | 7/2009 | Namineni et al. |
| 2009/0299522 A1 | 12/2009 | Savir et al. |
| 2010/0042255 A1 | 2/2010 | Boutin et al. |
| 2010/0076595 A1 | 3/2010 | Nguyen |
| 2010/0096399 A1 | 4/2010 | Ratnakar et al. |
| 2010/0256808 A1 | 10/2010 | Hui et al. |
| 2010/0270257 A1* | 10/2010 | Wachman ............... G06Q 10/10 215/228 |
| 2010/0305749 A1 | 12/2010 | Coe |
| 2011/0060448 A1 | 3/2011 | Gotou et al. |
| 2011/0160896 A1 | 6/2011 | Kim |
| 2011/0251850 A1 | 10/2011 | Stephens |
| 2012/0006708 A1 | 1/2012 | Mazur |
| 2012/0044054 A1* | 2/2012 | Hussain ............. G06K 7/10178 340/10.1 |
| 2012/0323360 A1 | 12/2012 | Lavin |
| 2012/0330460 A1 | 12/2012 | Henderson et al. |
| 2013/0006652 A1 | 1/2013 | Vahlberg et al. |
| 2013/0030566 A1 | 1/2013 | Shavelsky et al. |
| 2013/0134178 A1 | 5/2013 | Lu et al. |
| 2014/0007806 A1* | 1/2014 | Stanton ..................... G09F 3/00 116/201 |
| 2014/0263423 A1 | 9/2014 | Akdogan et al. |
| 2014/0278510 A1 | 9/2014 | McLean et al. |
| 2015/0090733 A1 | 4/2015 | Park |
| 2016/0039553 A1 | 2/2016 | Akdogan et al. |
| 2016/0039621 A1 | 2/2016 | Akdogan et al. |
| 2016/0042151 A1 | 2/2016 | Akdogan et al. |

OTHER PUBLICATIONS

"International Application Serial No. PCT/US14/029940, Search Report and Written Opinion mailed Oct. 28, 2014", 18 pages.
USPTO, "Application Serial No. 14/819,154, Non-Final Office Action mailed Jan. 12, 2016", 12 pages.
USPTO, "U.S. Appl. No. 14/216,162 Non-Final Office Action mailed Feb. 5, 2016", 24 pages.
International Searching Authority, "International Application Serial No. PCT/US15/43848, Search Report and Written Opinion mailed Dec. 28, 2015", 14 pages.

* cited by examiner

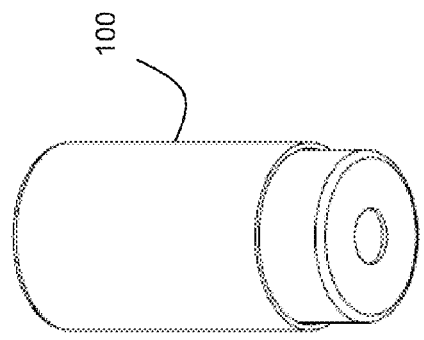
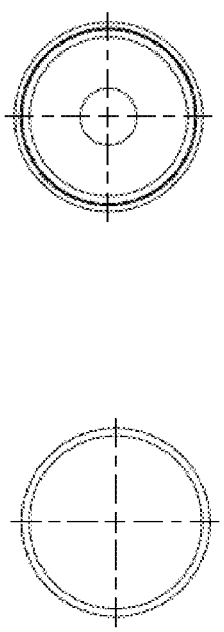
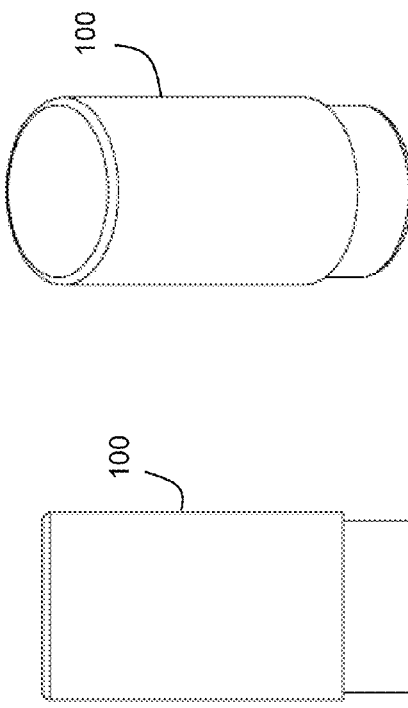

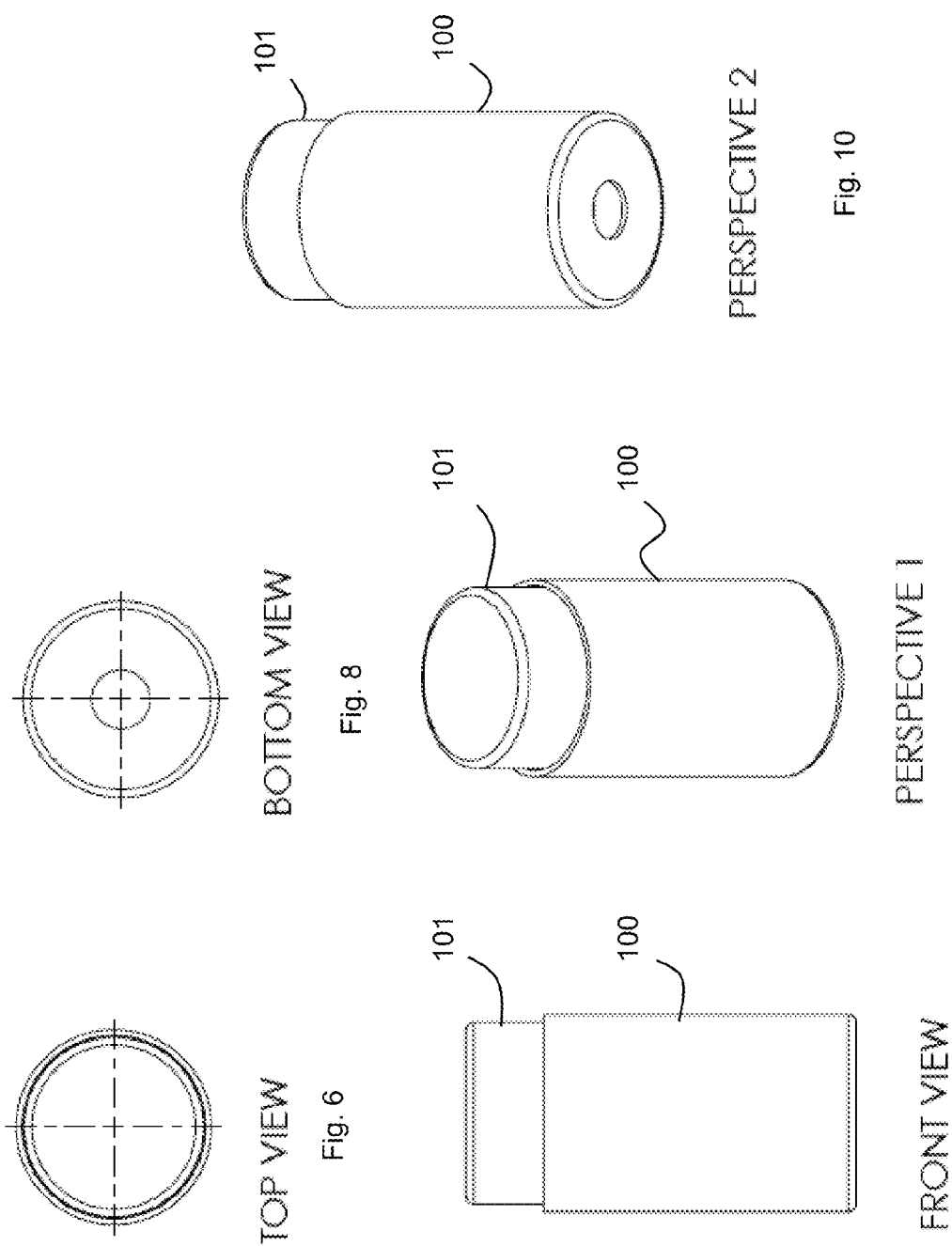

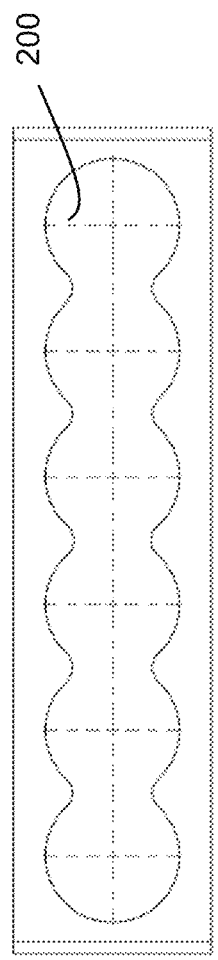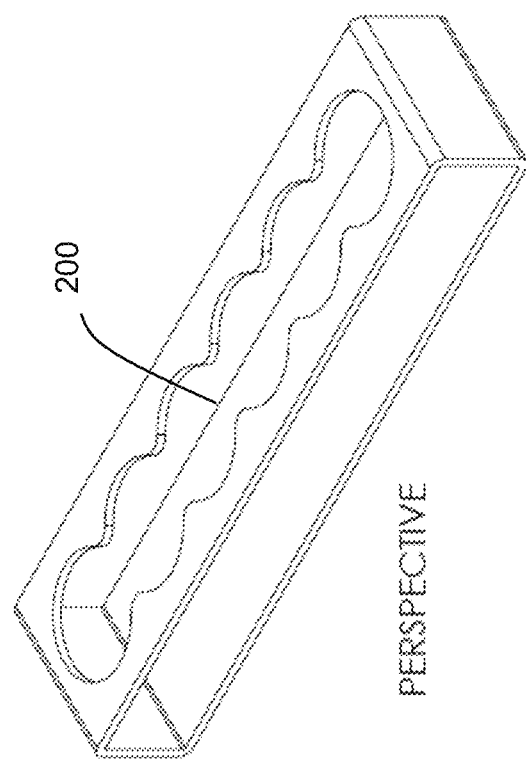
Fig. 16 TOP VIEW
Fig. 17 PERSPECTIVE

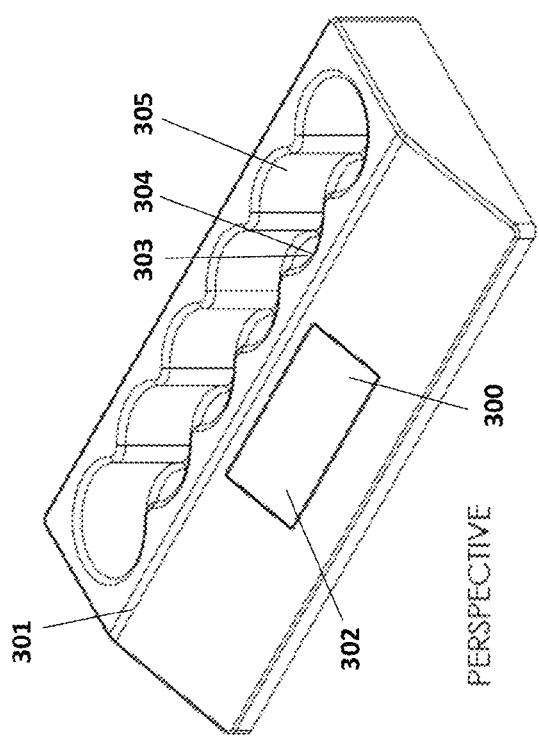
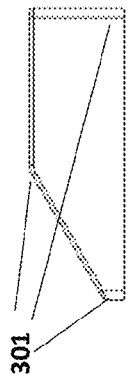
Fig. 20
Fig. 21
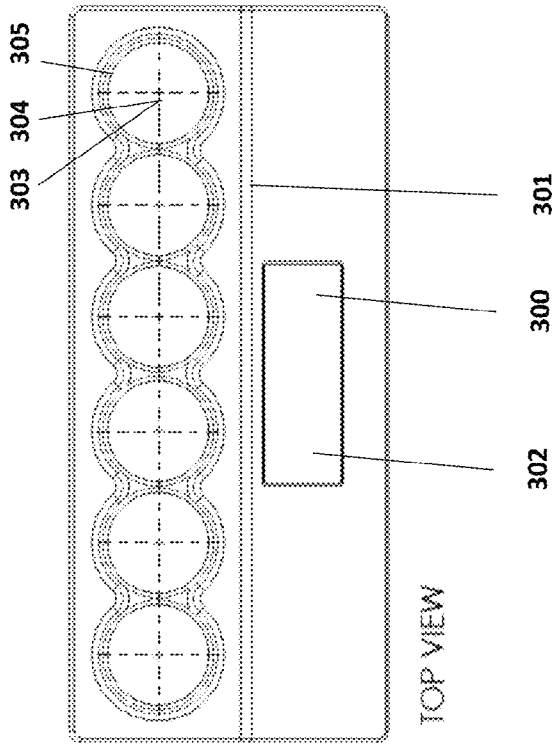
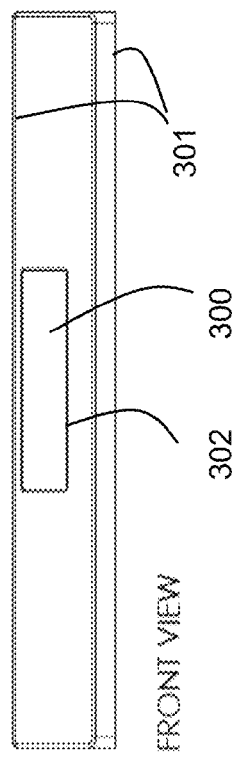
Fig. 18
Fig. 19

PERSPECTIVE

SIDE VIEW

TOP VIEW

FRONT VIEW

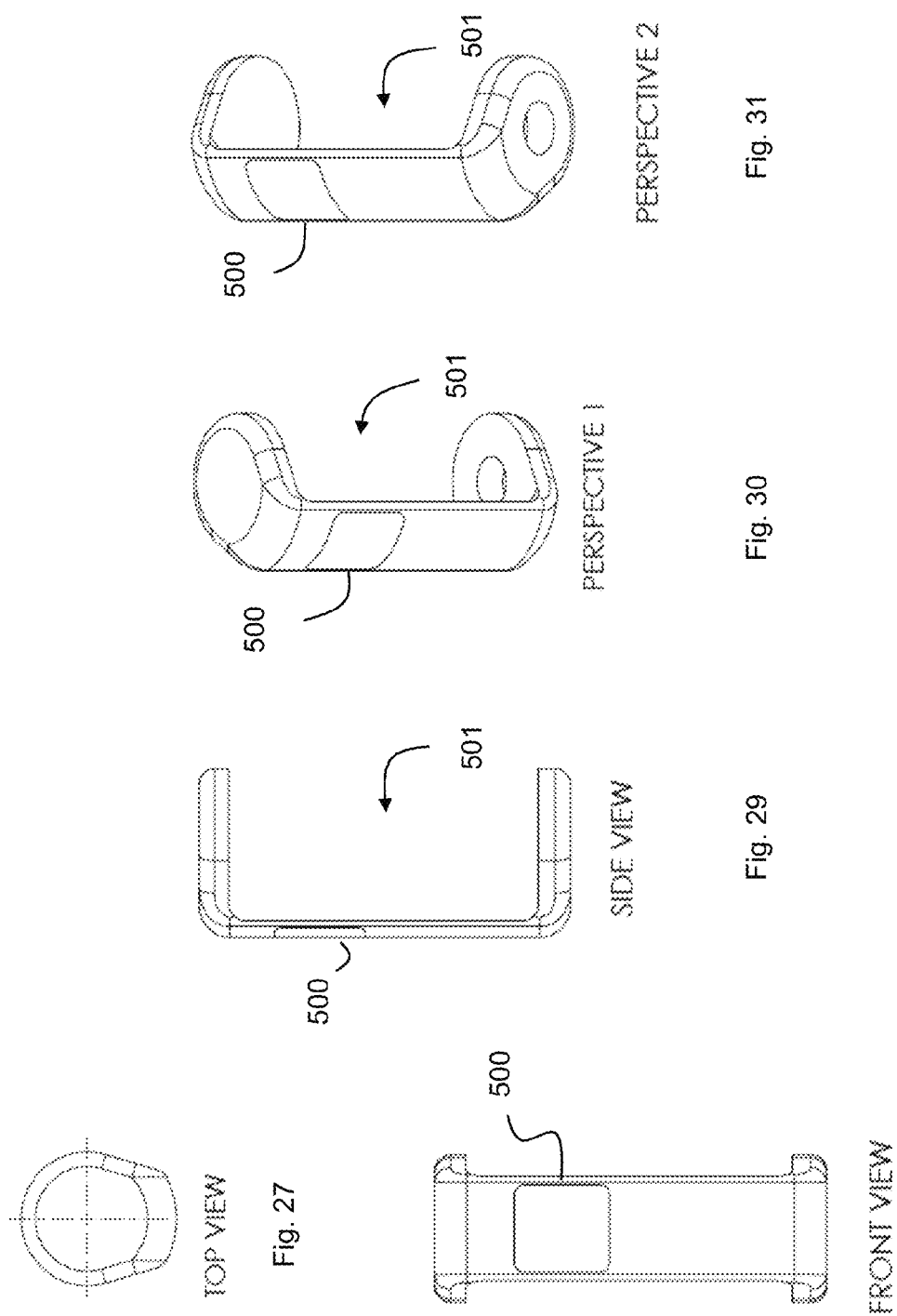

ively associated with each of the bases. Each of the dispensers may be configured to provide information to an associated one of the bases concerning a number and type of consumables contained therein. Each of the bases
MODULAR DISPENSING DEVICES FOR INFORMING A USER OF A NUMERIC AMOUNT OF CONSUMABLES AND A SCHEDULE FOR DISPENSING THE CONSUMABLES

RELATED APPLICATIONS

This application claims the benefit under 35 U.S.C. §119(e) of U.S. Provisional Application No. 61/800,973 filed on Mar. 15, 2013, the entire content of which is hereby incorporated by reference.

BACKGROUND

The disclosure relates to modular dispensing devices, and more specifically to dispensing devices having mechanical interfaces to couple to a container and a base.

SUMMARY

A dispensing device is improved through the inclusion of modular components, for example, mechanical interfaces to couple to a container and a base. The modular dispensing device may also include communication systems related to the container and the base. Specifically, the modular dispensing device may receive information such as the contents of the container (e.g., quantity, identity, etc.) and a schedule for dispensing the contents. Using this information, the modular dispensing device may control the dispensing of the contents of the container.

In one aspect, a device includes a first mechanical interface configured to removably and replaceably couple to a container of consumables, and a first communication interface configured to receive data from the container relating to a number of consumables in the container when the device is coupled to the container through the first mechanical interface. The device may also include a second mechanical interface configured to removably and replaceably couple to a base, and a second communication interface configured to receive a schedule for dispensing the consumables from the base when the device is coupled to the base through the second mechanical interface. Additionally, the device may include a memory that stores the number of consumables and the schedule, and a user input that is actuatable by a user to dispense one of the consumables from the container.

In another aspect, a computer program product includes computer executable code embodied in a computer readable medium that, when executing on one or more computing devices, performs the steps of: detecting an insertion of a cartridge containing consumables into a base; reading a numeric amount of the consumables from the cartridge and communicating the numeric amount to the base; and reading a schedule for medication from the base and communicating a portion of the schedule relating to the consumables in the cartridge to the cartridge.

In yet another aspect, a system includes a server having a memory that stores schedules for dispensing consumables to a plurality of users, where the server provides an interface for updating one of the schedules. The system may also include one or more bases, each coupled in a communicating relationship with the server and each storing at least one of the schedules, and one or more dispensers of consumables removably and replaceably associated with each of the bases. Each of the dispensers may be configured to provide information to an associated one of the bases concerning a number and type of consumables contained therein. Each of the bases may be configured to dispense consumables from one of the dispensers according to one of the schedules stored thereon.

In another aspect, a computer program product includes computer executable code embodied in a non-transitory computer-readable medium that, when executing on one or more computing devices, performs the steps of: receiving a schedule for dispensing consumables to a user; receiving an association of a base with the user; transmitting the schedule to the base, where the base is operable to execute the schedule by providing notifications to the user and by dispensing unit form consumables from each of one or more containers removable from and replaceable to the base; receiving data from the base characterizing a type and quantity of consumables in each of the one or more containers; and executing the schedule from the base.

BRIEF DESCRIPTION OF THE DRAWINGS

The foregoing and other objects, features, and advantages of the devices, systems, and methods described herein will be apparent from the following description of particular embodiments thereof, as illustrated in the accompanying figures, where like references numbers refer to like structures. The figures are not necessarily to scale, emphasis instead being placed upon illustrating the principles of the devices, systems, and methods described herein.

FIGS. 1-5 show a cartridge with a dispensing trigger.
FIGS. 6-10 show a cartridge with dispensing trigger.
FIG. 16 shows a holder.
FIG. 17 shows a holder.
FIG. 18 shows a base.
FIG. 19 shows a base.
FIG. 20 shows a base.
FIG. 21 shows a base.
FIG. 27 shows a clip for dispensing items.
FIG. 28 shows a clip for dispensing items.
FIG. 29 shows a clip for dispensing items.
FIG. 30 shows a clip for dispensing items.
FIG. 31 shows a clip for dispensing items.

DETAILED DESCRIPTION

Figure 12:
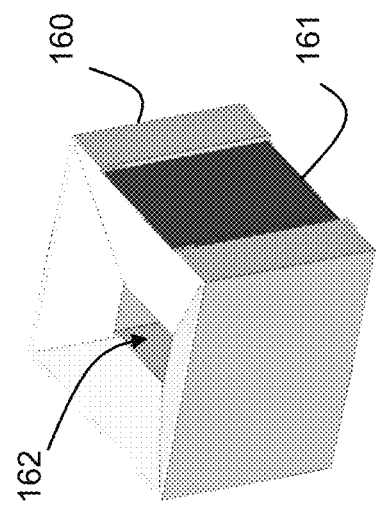
FIG. 12 shows a spring-slider dispensing mechanism.
Figure 11:
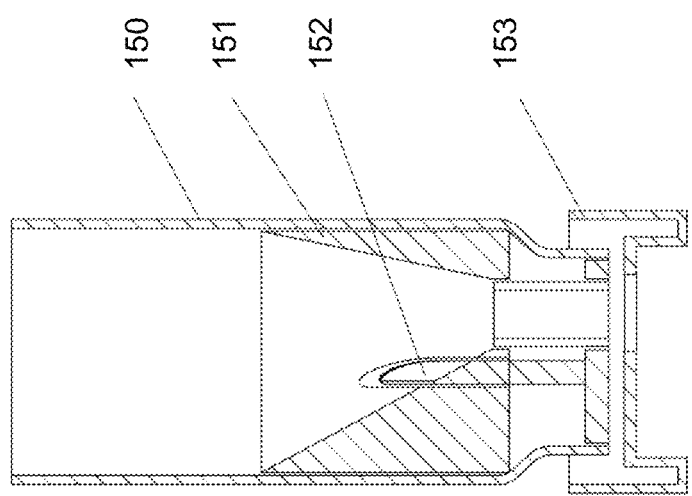
FIG. 11 shows a palm-press dispensing mechanism.
Figure 14:
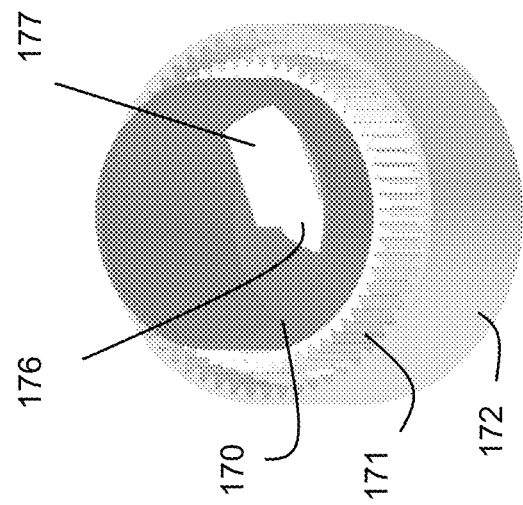
FIG. 14 shows a rotational dispensing mechanism.

All documents mentioned herein are hereby incorporated by reference in their entirety. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context. Thus, the term "or" should generally be understood to mean "and/or" and so forth.

Recitation of ranges of values herein are not intended to be limiting, referring instead individually to any and all values falling within the range, unless otherwise indicated herein, and each separate value within such a range is incorporated into the specification as if it were individually recited herein. The words "about," "approximately," or the like, when accompanying a numerical value, are to be construed as indicating a deviation as would be appreciated by one of ordinary skill in the art to operate satisfactorily for an intended purpose. Ranges of values and/or numeric values are provided herein as examples only, and do not constitute a limitation on the scope of the described embodiments. The use of any and all examples, or exemplary language ("e.g.," "such as," or the like) provided herein, is intended merely to better illuminate the embodiments and does not pose a limitation on the scope of the embodiments. No language in the specification should be construed as indicating any unclaimed element as essential to the practice of the embodiments.

In the following description, it is understood that terms such as "first," "second," "above," "below," and the like, are words of convenience and are not to be construed as limiting terms.

The drawings are provided as an aid to understanding the following disclosure. The drawing are not necessarily to scale, and are not representative of preferred embodiments of the subject matter described herein unless otherwise stated to the contrary or clear from the context.

While the following description provides detailed embodiments of methods, systems, and devices for managing consumable items, it will be understood that the specific embodiments described herein are provided by way of example and not limitation, and that various aspects of this disclosure may have additional applications independent from those that are described. For example, the systems and methods described herein may be adapted to any environment where liquids, solids, powders, suspensions, and the like are controllably dispensed on any predetermined or ad hoc schedule such as a chemical, pharmaceutical or life sciences laboratory or a packaging facility for custom deliverables. All such variations are intended to fall within the scope of this disclosure.

DEFINITIONS

The term "dispensable" and related terms such as "dispensable unit" are intended to refer broadly to an item, combination of items, composition, component, material, compound or the like that can be dispensed in unit or continuous form.

While a "dispensable" may be any item that can be dispensed, the term "consumable" or "consumable unit" is intended to refer to dispensables that are intended to be consumed by a user. Consumables are intended to include a wide array of ingestible consumable items and form factors for same. For example, consumable units may include one or more of pills, capsules, tablets, chewables, lozenges, dissolvables, sprinkles, dissolve-in-mouth micro-capsules, orally disintegrating tablets, chewable tablets (including jelly beans, gummies, and the like), gums, and so forth, as well as continuous form consumables such as liquids or powders, solutions, pastes, and suspensions, and combinations thereof.

The consumables may also or instead include items provided as free powders, powder sachets, liquids, liquid sachets, vials, cups, cases, other storage forms, and so forth. More generally, the consumable units may be any composition for consumption in bulk, individual, individual pre-packaged, group pre-packaged and/or mixed item package form. For bulk form compositions, the "consumable unit" may be a predetermined portion for dispensing such as a teaspoon of liquid, a number of pills, a milligram of powder or the like, or a similar predetermined portion for dispensing or mixing into a compound locally created for dispensing prior to or after dispensing.

Similarly, the content of each consumable unit may vary significantly and may include but are not limited to prescription medication, non-prescription or over-the-counter medication, nutritional supplements, vitamin supplements, mineral supplements, veterinary medications, veterinary nutritional supplements, and so forth. Consumable units may also or instead include food and other items such as sugar, seeds, candies, snacks, pet treats, or other foods and the like, as well as any other pharmaceuticals, nutraceuticals, or other consumable items not identified above. These consumables that are intended to be ingestible are also referred to herein as "ingestibles" or "ingestible units."

While consumables may include items for consumption in the convention sense of ingestion as described above, consumables may also or instead include disposable items or the like that are intended for one time use. Thus, as used herein a "disposable" may be any consumable intended for a use other than ingestion. This may, for example, include disposable medical items such as dressings, bandages, Band-Aids, gauze, syringes, thermometers, individually packaged units of antibacterials and the like, as well as other items such as hearing aids, contact lenses and so forth that can be dispensed in individual units for one time use. This may also or instead include continuous form items not intended for ingestion including personal care items such as toothpaste, toothpicks, soap, sanitizer, moisturizer, cotton swabs and the like, as well as other household items such as glue, batteries, latex gloves, and so forth. All such disposables may be a form of consumable as those terms are used herein, and consumables may similarly be a form of dispensable.

It will be understood that while the foregoing terms (dispensable, consumable, ingestible, disposable) may be variously used in this disclosure to describe embodiments of the invention, the inventive concept generally applies to any and all such dispensables, and any description of one type of dispensable will be understood to refer to all such dispensables except where specifically noted to the contrary. Thus for example, a container for consumable items will be understood to similarly teach a container for dispensable items, a container for ingestible items, and a container for disposable items. As another example, a schedule for delivery of a medical prescription will be understood to similarly teach a schedule for delivery of any dispensable, ingestible, consumable, and disposable, with suitable modifications being readily apparent to one of ordinary skill in the art.

Another term used frequently in the following description is "schedule." As used herein, this is intended to refer to any time-based or event-based regime for using dispensables. This may, for example, include a single/one-off/ad-hoc trigger or time/date, or this may include any number of one time, periodic, and/or recurring events. Thus, for example, a schedule may specify an event once per day for one week, or three times a day for two weeks, or twice a day indefinitely. It will also be appreciated that a schedule may include events defined with respect to specific days or times of day, or events that are dependent on some other event. Thus for example, a schedule may indicate an event that is to occur once a day before breakfast, or three times a day after meals. While dosing regimens for medicines, nutritional supplements and the like are contemplated as schedules, it will be understood that a schedule may be provided for any dispensable contemplated herein. In general, a schedule may be a data structure stored in a memory in any suitable form for use in managing dispensables as contemplated herein, and it will be appreciated that a user may maintain any number of independent or interrelated schedules, and that a schedule may conversely specify events for any number of users, all without departing from the scope of this disclosure.

It will also be observed that a variety of terms are used to describe the hierarchical and modular structural components of a dispensable management system such as containers, cartridges, dispensers, clips, and bases. It should be understood that these are terms of convenience only and are not intended to be limiting. Instead, a wide range of system architectures are contemplated, including various distributions of processing circuitry and hardware that performs various tasks such as scheduling, notification, communications, dispensing, and so forth. Thus, for example, mechanical systems for dispensing dispensable may be integrated into a base, a dispenser, a clip, and/or a container. Similarly, processing for maintaining schedules, monitoring container contents and the like may be integrated into a base, a dispenser, a clip, and/or a container. More generally, a reference to any component of a dispensing system as contemplated herein should not be understood to require any particular hardware, processing circuitry, or functionality, and similarly should not be understood to exclude any particular hardware, processing circuitry, or functionality except where specifically stated otherwise.

Thus as used herein, the term base may refer to a unit that provides a simple mechanical holder for a number of dispensers or the like. In another aspect, the base may be a dispensing base that includes dispensing infrastructure shared by any number of containers, dispensers, and the like, such as a common chute and dispensing hardware for multiple dispensables. In another aspect, the base may use dispensing hardware from each dispenser or the like attached thereto, while providing enhanced functionality such as scheduling and notification based on an associated user and attached dispensers. In another aspect, a base may be configured for use with a single dispensable, while providing integrated scheduling, notification and the like as contemplated herein. All such variations are intended to fall within the meaning of a "base" as that term is used herein.

In a similar fashion, a dispenser, cartridge, or clip may provide any level of integration with respect to containing dispensables, dispensing dispensable, managing schedules, providing notifications and so forth. At the same time, any particular function related to the managed system may be performed by a dispenser, cartridge, clip, or base, or be distributed in any useful manner among these modular components of the system. Thus the use of any one of these terms in the following description should be understood to contemplate all such devices, except where a specific form of cooperation between two such components is explicitly described.

Without limiting the generality of the foregoing, it is broadly contemplated that a container may hold dispensables in bulk or unit form. A cartridge or dispenser may house a container and provide or support dispensing functions. A base may provide a desktop unit or the like to removably and replaceably hold any number of containers, cartridges, or dispensers, and may also provide various degrees of augmentation to management of dispensables. A clip may also optionally be employed as an electromechanical interface between a base on one hand, and any container, cartridge, or dispenser on the other.

Cartridge of Consumables

A cartridge may be a single-dose, single-unit, multi-dose, multi-unit or continuous/burst dispensing container, which may be fully disposable, partially disposable, or fully reusable.

The cartridge as described may provide a machine input to interact with one or more configuration devices, such as a holder, a base, a dispenser and/or a clip. A holder may store cartridges or other attached devices. A base may manage, dispense and/or store consumables from attached cartridges or other devices. A base may manage, dispense and/or repackage consumables from attached cartridges or other devices. A clip may be a lightweight, mobile attachment to one or more cartridges.

The cartridge may have an aesthetic design which may have either a polygon or a round base, where one or more reservoirs 100 may hold the consumable units. The cartridge may have multiple reservoirs, where reservoirs may accept the same or different media/media properties.

There may be a single exterior cartridge form for all consumable media within, regardless of size and properties of media (e.g. small pills vs. large capsules vs. liquid sachets vs. free powders vs. liquids).

Single dose dispensing may be achieved in one embodiment by depressing a button horizontally on one of the side faces; in another embodiment by pressing the entire top section of the cartridge down into the user's palm (FIG. 1, FIG. 2, FIG. 3, FIG. 4 and FIG. 5); in another embodiment by depressing a button near the top 101 (FIG. 6, FIG. 7, FIG. 8, FIG. 9 and FIG. 10).

The cartridge may offer similar protection characteristics to existing pill bottles (e.g. against moisture), as all or some of the following may apply: (1) Use of same or similar plastic materials (2) Tamperproof aluminum foil seal on reservoir (3) Cotton wool inside reservoir to prevent transportation damage to media (4) Desiccant for moisture management, which may be in a small bag in the reservoir or in a separate desiccant chamber.

The desiccant may be part of a functional desiccant component that may perform functions beyond desiccation, including but not limited to communication with the clip, base, dispenser or other devices (via RFID, NFC or other short or long range communication technologies embedded within functional desiccant) and consumable volume detection (via capacitance fields).

The reservoir may have a door on one of its faces, which could allow for users to add or remove any number of consumable units, and which may have a visual indication upon it that warns users not to insert incompatible media. In one embodiment, this door may be a simple face that swings open on a hinge once a latch is release. In another embodiment, this door may be a face cap-like piece that snaps into place and may or may not be removable.

The label may be on any of the faces of the cartridge, to ensure visibility when in the clip, base and dispenser.

The cartridge may have a specific lock-and-key connection/attachment (on any of its faces/sides) to the clip, holder, base or dispenser. In one embodiment, this lock-and-key connection may be 3 differently-sized prongs distributed horizontally and asymmetrically about the vertical axis of the cartridge. In another embodiment, this connection may be a set of electromagnets that may be activated by the clip, dispenser, base or holder upon the cartridge touching. In yet another embodiment, this connection may be a combination of prongs and electromagnets.

The cartridge may have electrical contacts/touchpoints (which connect to an EPROM/EEPROM embedded within), NFC or RFID sticker, or QR code on label/exterior for communication with the clip, base or dispenser.

Moving parts of dispensing mechanisms may have unique color system/aesthetic/branding.

The reservoir may be transparent or translucent or have a window (a hole or a transparent material) on one of its faces to allow users to view rough proportion of consumables remaining in the cartridge, or may have a physical display of a counter showing exact number of consumable units remaining.

The reservoir may have copper foil or plate on some faces, either implanted within the reservoir form or within a sticker that is attached to the reservoir, in order to enable dose counting via capacitance field measurement.

The reservoir may hold any number of consumable units depending on size, or one continuous form of consumable media (where consumables may include, but are not limited to, pills, capsules, free powders, powder sachets, liquids, liquid sachets, sprinkles and dissolve-in-mouth micro-capsules). The reservoir may hold any category of unit-form or continuous-form consumables, including but not limited to over-the-counter medication (e.g. Cold/Cough/Allergy, Pain/Analgesic, Gastro-Intestinal, Sleep, Eye Care, Weight Control, Feminine Hygiene), Vitamins/Minerals/Supplements (e.g. multi-vitamins, energy supplements, one-a-days, Calcium, fish oils, men's/women's health pills, combination energy/nutrition/health products), prescription medications (e.g. Lipitor, other brands, generics), veterinary medications/nutritional supplements.

While a single reservoir is depicted, it will be understood that a cartridge may have any number of reservoirs, and may be configured for independent dispensing from each reservoir, or dispensing in combination from multiple reservoirs. The reservoirs may be configured for either or both of similar or different media types.

The cartridge may have one of several single-unit dispensing mechanisms, of which 5 are listed here: (1) Palm-press: User presses cartridge into palm with their other hand, and a unit is dispensed into the palm, based on durable agitator and asymmetrical chute to prevent jamming and mis-dosing (2) Spring-slider: User pulls trigger, one unit falls out, based on durable cavity & agitating wedge technique to prevent jamming and mis-dosing (3) Rotational: User twists exterior cylinder, units align within, every 120 degrees one unit falls out; unit alignment prevents jamming and mis-dosing (4) Blister-doser: User actuation pushes blister strip forward and severs material to dispense single blister unit (5) Thumb-press: User depresses top of cartridge with thumb, and one unit is presented at the bottom of the cartridge. 3 of these mechanisms are explained in more detail below.

For the palm-press mechanism design there may be four parts. The container 150 may connect to the chute 151 using a snap retaining feature. The agitator 152 may be attached to the cap 153 via a similar snap retaining feature. The agitator 152 and cap 153 may move in relation to the container 150 and chute 151. When the user presses the cartridge against their palm, the agitator 152 and cap 153 may move up into the chute 151. The resulting agitation of contained units facilitate units dropping down and moving through a hole within agitator 152 and cap 153 to exit at the base the through the cap. The chute 151 is asymmetrical such that its bottom hole is not in the center, and this, combined with the off-center asymmetric shape of the agitator 152, may prevent jamming due to concentration of units at the cartridge center (from uniform gravitational pull). The cap 153 may contain a rocker mechanism that can fit only one unit.

Figure 13:
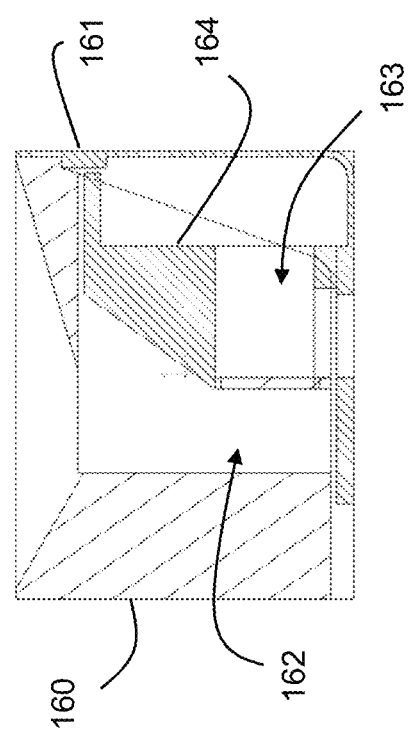
FIG. 13 shows a spring-slider dispensing mechanism.

For the spring-slider mechanism design, there may be two pieces—the body 160 and the arm 161—which may be connected (e.g. by glue or by molding entire Cap as one piece) at the hinge. The user may manually push the arm 161 horizontally in towards the center of the body 160. This sliding action aligns the arm's hole with the body's chute, allowing for unit release. Units in the body 160 may be aligned with their longest side vertical, due to the tight fit of the chute 162. Pushing the arm 161 may also translate the agitator box 163 into the chute 162, which may separate the unit to be dispensed from other units. The agitator ramp 164 on top of the agitator box 163 may push these other units back up towards the reservoir (not shown, but vertically above the mechanism shown in FIG. 13 Error! Reference source not found.) with each push of the arm 161. Childproofing may be enabled by a latch on the body 160 or tabs that must be squeezed by the user for the arm 161 to freely move, or another method. The body 160 may be attached to the reservoir by a snapping mechanism. In some embodiments the mechanism as a whole may be operated using one finger on one hand only.

Figure 15:
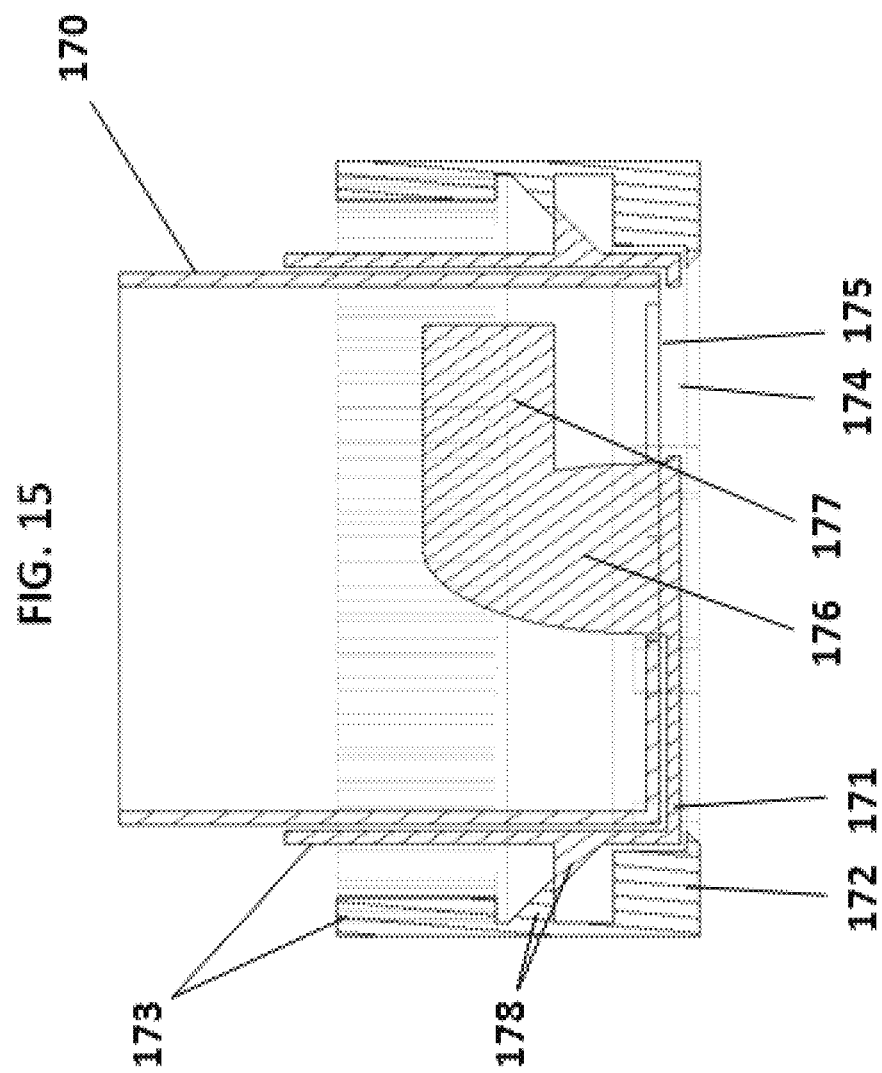
FIG. 15 shows a rotational dispensing mechanism.

For the rotational mechanism design, there may be three pieces that move relative to each other. These pieces may be set one inside the other: the inner layer 170, the middle layer 171 and the outer layer 172, of which the inner layer may be connected via screw thread to the reservoir (not shown, but vertically above the mechanism shown in FIG. 15). The user may rotate the outer layer 172. This action may be childproofed; the outer layer 172 may have gear teeth 173 that (when the outer layer is squeezed hard enough) make contact with the gear teeth on the middle layer 173, allowing the twisting of the outer layer to rotate the middle layer 171—but if the user does not squeeze, the gears do not engage. The base/dispenser may bypass this squeezing by engaging the middle layer gear teeth 173 directly using an actuation arm. The rotation of the middle layer 171 may align the middle layer hole with the inner layer holes 175 1, 2 or 3 times per full revolution (depending on the number of inner layer holes). Alignment of holes 174 and 175 may allow units to exit the cartridge. Single unit dispensing may occur at each alignment due to inner layer pins adjacent to each inner layer hole which prevent other units following the first as it exits. A parabolic center protrusion 176 may be connected to the middle layer 171 and may tend to align units around the circumference of the bottom of the inner layer 170. There may be an agitator arm 177, which may be connected to the center protrusion 176 and may sit above the middle layer hole 174, and whose purpose may be to push one unit towards the exit hole while forcing others away, in other words agitating them. There are protruding rings 178 on the middle layer and outer layer which may allow the middle layer 171 to snap irreversibly onto the outer layer 172 during manufacture.

All above single-dose dispensing mechanisms may work universally with all unit sizes, in one of several ways such as the 2 following: (1) For each grouping of unit size/shape, there may be slightly different mechanism dimensions (achieved by slight variations on the mold tooling and manufacturing line), though the exterior form does not change at all (2) There may be one universal mechanism with a small collar within that is adjusted on the packaging line for different groupings of unit size/shape.

All above single-dose dispensing mechanisms may allow for a combination of gravity fed and powered dispensing of consumables.

The same mechanism may be used when the cartridge is used independently or in concert with an attached clip, base or dispenser.

Actuation may be childproof, for example in the following way: before trigger can be pulled, side or top tab(s) must be depressed.

Besides the single dose dispensing mechanism, user may access consumable media by opening the door in reservoir and dispensing in bulk.

Each single dose dispense actuation may trigger a dose counter mechanism to increment. The dose counter may be a rotating horizontal or vertical dial. The cartridge may have a window or opening through which the dose counter's current count is visible. The dose counter's count may represent one of the following: (1) Total number of units taken out since opening (2) Total number of units remaining Reliable counting may be enabled in the following manner: (1) Dose exit cavity may have a rocker mechanism that does not engage if a dose is not inside it, in other words, if the user actuates the dispenser but no dose comes out, the dose counter may not increment (2) Rocker mechanism at exit may not engage until the dose has left it, in other words, if the user does not extract the dispensed dose (assuming the dose has not left the rocker mechanism), the dose counter may not increment.

Digital information may be stored on QR code, in NFC sticker, in EPROM/EEPROM chip embedded in cartridge form or on machine-readable imprint on the dose counter. Stored information may include, but is not limited to (1) SKU # (2) Expiration date (3) SKU name (4) Milligrams per dose of SKU (5) Weight of empty SKU cartridge (6) Weight of single unit of SKU consumable (7) SKU warnings (8) SKU directions and guidance (9) Unique cartridge ID. There may be a specific format/encoding for digital storage of above information.

The cartridge may have powered electronics onboard.

The cartridge may have following display methods, which may be multi-colored or monochromatic: non-touch screen, touch screen, LED screen, LCD screen, e-ink/e-paper screen, smartphone, desktop computer and tablet.

The cartridge may have LEDs/speakers/vibrational motors that provide audiovisual (both human-audible and not) and vibrational feedback based on input from bases, dispensers and clips.

The cartridge may have several ports for input/output communication, including but not limited to wireless/cellular internet (e.g. Wi-Fi, WiMAX, 3G, 4G, 4G LTE, RFID, NFC), wired internet (e.g. Ethernet), USB, media card (e.g. SD, CF, xD) and displays (e.g. HDMI, VGA, DVI, DisplayPort). The cartridge may automatically communicate or connect with cloud (see later section on cloud layer) via its communication ports.

Based on data from wireless access routers/towers/etc., or onboard GPS, or user input, the cartridge may automatically broadcast its location to cloud, or any base, dispenser, clip, cartridge or compatible smart device.

The supply chain may involve manufacture of cartridge using standard molding and assembly lines/practices, with different molds for any cartridge parts that SKU-specific or SKU-family-specific. Cartridge data may be printed onto cartridge via proprietary format QR code or programmed EPROM may be implanted into cartridge plastic. Standard high speed packaging/bottling lines may pack pills, capsules, powders, powder sachets, liquids and liquid sachets of any weight and size into a cartridge. The supply chain may handle repacking of mail order pharmaceuticals into cartridges, and may interface with mail order pharmacies to acquire Rx product.

In one aspect a container such as any of the containers above may be provided without surrounding electromechanics for dispensing dispensables. This may, for example, be a simple container for dispensables that can be inserted into and removed from a dispenser such as any of the dispensers described above, or inserted into and removed from a base or the like that provides dispensing functionality for the container.

Simple Holder of Attachables

A holder may store attached cartridges and loaded/empty clips (which among other devices may be referred to as attachables).

The holder may have a welcoming and professional aesthetic design.

The holder may be powered or unpowered.

The holder may have modular design that enables add-on capability to be attached, as well as certain modules to be simply removed for easy maintenance/repair.

The holder may have internal shock mounts to prevent consumable disturbance and damage. Holder may have secrecy door or electrochromatic door for privacy of stored consumables.

The holder may store one or multiple attachables in separate sockets 200 (number of sockets depends on model of holder) or via one long platform/shelf that can accommodate all attachables. The holder may connect to attachables via a lock-and-key or magnetic attachment (as described earlier), which may be universal across all cartridges and clips.

Smart Base for Attachable Management

A base may manage, dispense and/or store consumables from attached cartridges and loaded/empty clips (which among other devices may be referred to as attachables), and communicate with cloud.

The base may have a welcoming and professional aesthetic design.

The base may be powered by line power or by a rechargeable/disposable internal battery. In an embodiment with line power, a battery may enable the base to run on backup power in the event of a power outage, which allows the continued use and/or extraction of consumables within. This may be useful, for example, in scenarios where the consumable is a patient-necessitated prescription medicine.

The base may have a modular design that enables add-on capability to be attached, as well as certain modules to be simply removed for easy maintenance/repair.

The base may have internal shock mounts to prevent consumable disturbance and damage. The base may furthermore have an accelerometer, which can detect large forces and accelerations on the device. Upon such detection, the base may perform additional safety and protection functions to ensure that consumables are not disturbed or damaged, including but not limited to physical lockdown, activation of internal dampeners, alarm sounding, LED flashing, wireless notification, and emergency service alerting.

The base may have one or more secrecy doors or electrochromatic doors for privacy of stored consumables.

A fingerprint scanner (CMOS sensor) 300, face recognition camera, or other biometric identification system(s) may be present.

The base may have LEDs, screens, speakers and vibrational motors 301 for multi-colored audiovisual (both human-audible and not) and vibrational notifications and feedback (including but not limited to consumption alerts, scheduled alerts and connection of an empty clip).

The base may have following input methods: touch of touchscreen 302, pressing of button, sliding finger over non-press button, voice commands, touching of fingerprint reader 300, use of NFC or RFID for proximity detection. Base may have following display methods, which may be multi-colored or monochromatic: non-touch screen, touch screen, LED screen 302, LCD screen 302, e-ink/e-paper screen 302, and mirroring to any external screen including that of a smartphone, desktop computer, and tablet. The base's e-ink/e-paper screen 302 may be sub-divided so that updates of one division's screen are triggered by events relating to only one attached cartridge.

Figure 22:
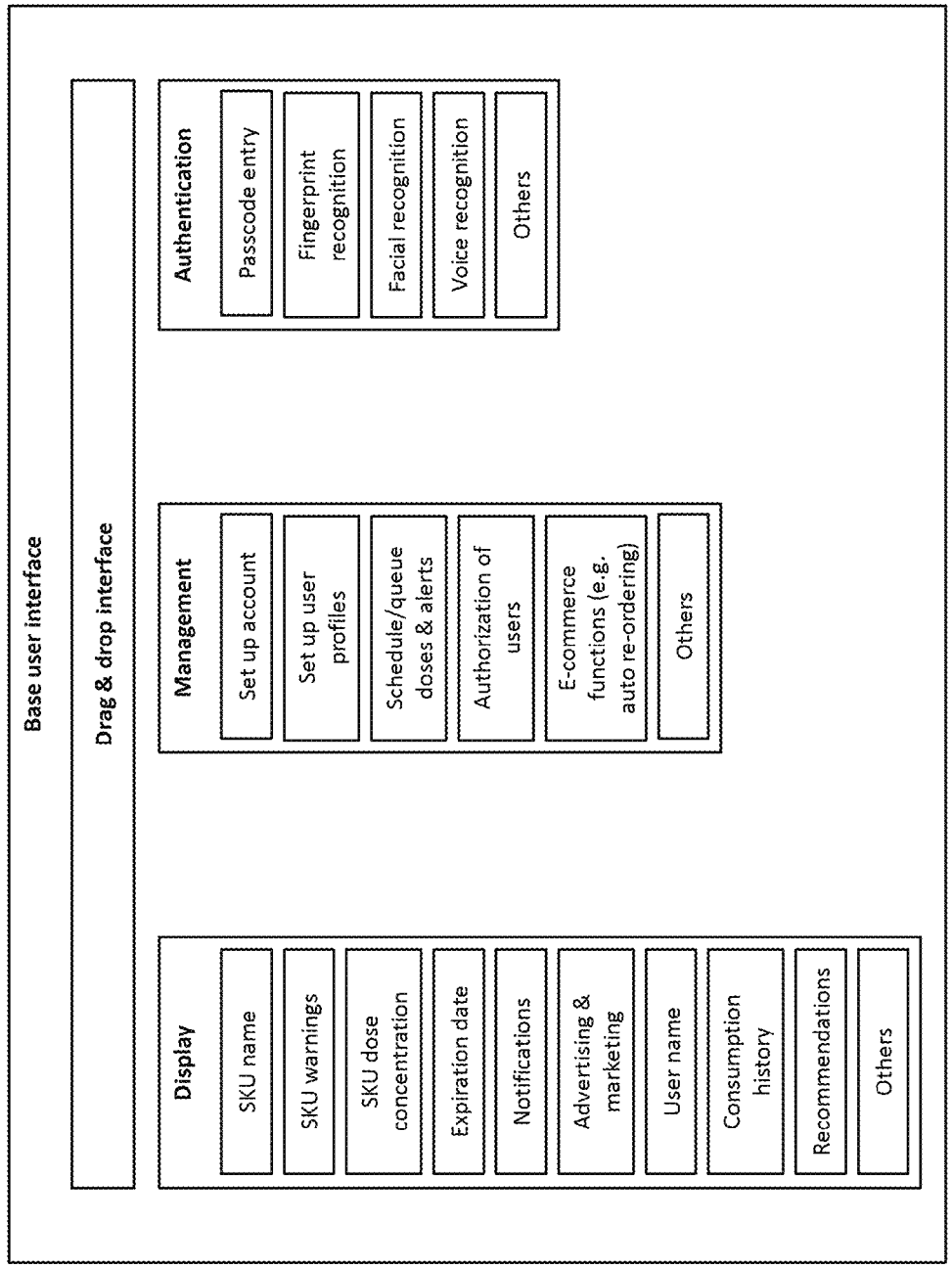
FIG. 22 illustrates functions of a user interface for managing dispensables.
Figure 25:
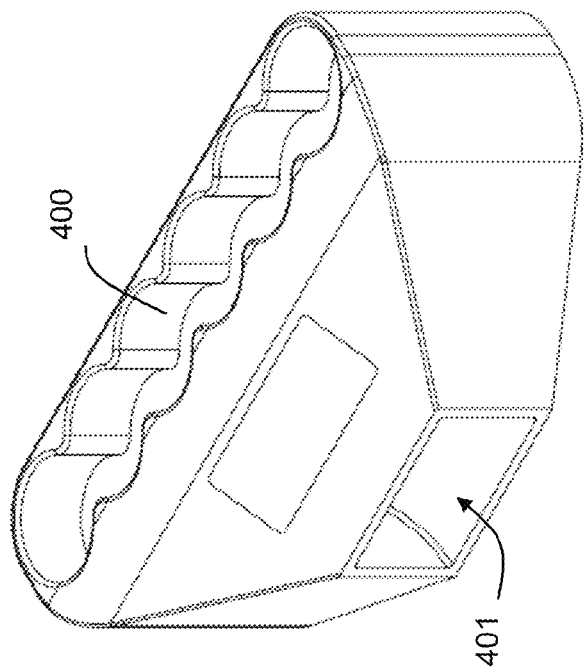
FIG. 25 shows a base for dispensing items.
Figure 26:
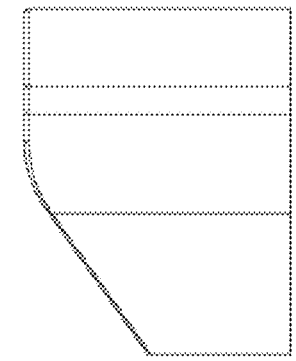
FIG. 26 shows a base for dispensing items.
Figure 23:
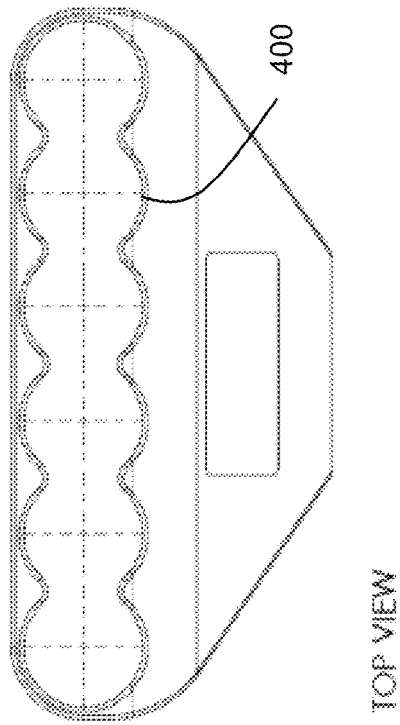
FIG. 23 shows a base for dispensing items.
Figure 24:
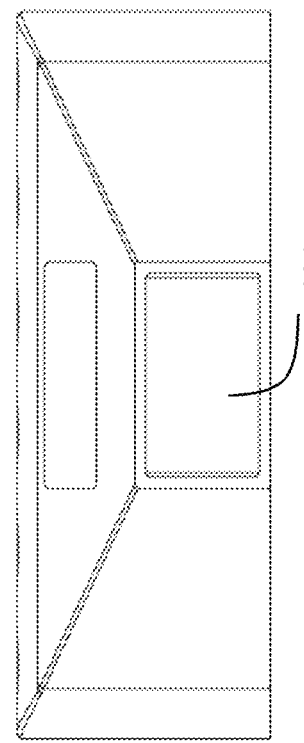
FIG. 24 shows a base for dispensing items.

The base's user interface functions (some represented in FIG. 22) may be as follows. The base's display may show/denote a wide variety of information, including but not limited to consumable SKU name, SKU warnings, SKU dose concentration, expiration date, notifications (e.g. need for replacement/reorder, non-adherence, software updates), advertising/marketing, user name, user consumption history (numerical or visual/chart-based), user recommendations, consumables consumed and consumable quantity remaining in cartridges. The base may allow users to set up an account (via cloud), and/or set up user profiles for each individual user. The base may allow users to schedule doses and set alerts, alarms and notifications via the interface (may also be done via cloud). The base may enable authentication in one or more ways, including but not limited to the following: (1) Passcode entry (2) Fingerprint recognition, via fingerprint scanner (3) Face recognition (via mounted camera) (4) Voice recognition. Authentication, authorization and usage permissions for each specific attachable may be enabled, disabled or overridden by account owners for specific users (may also be done via cloud). Users may set up e-commerce functions (e.g. automatic reordering) for specific cartridges on the base (may also be done via cloud). The base may use a "drag-and-drop" interface experience, where an account owner may drag images (representing consumable units or usage permissions, for example) onto images of users, where these images may be a default stock image or a user-uploaded image (via cloud). Example applications of this "drag-and-drop" interface on the base include the following: (1) Dragging consumable units to users, when base detects that a cartridge previously removed has been replaced on the base but with fewer consumable units than before (see description below of enumerator mechanism below) (2) Dragging and bestowing usage permission for specific SKUs/cartridges to users (3) Copying a dosage/alert schedule from one user to another (4) Dragging images of SKUs onto users to purchase or reorder or setup automatic reordering. Upon user input or after defined timeout, the base may enter sleep mode to minimize power consumption.

The base may include a reader mechanism 303 which may read digital information from attachables. The base's reader mechanism may function in several ways, including but not limited to QR code reader (CMOS sensor), NFC or RFID sensor/reader, and touching of the base's electrical contacts to electrical contacts on attachable. The base's reader mechanism may be able to read from all attachables (i.e. 1 reader mechanism for all or individual mechanisms for each attachable). The base's reader mechanism may be able to distinguish one attached attachable from another, as well as from unattached attachables.

Communication with attachables may be two-way, in which an attachable may also receive and store information from the base. The base may communicate with a specific attachable to instruct it to glow, make a sound or vibrate, potentially based on the following stimuli: (1) Cartridge consumables are depleted (2) Cartridge consumables have expired (3) The scheduled time to consume cartridge consumables has arrived (scheduling is set via cloud). The base may have several further ports for input/output communication, including but not limited to wireless/cellular internet (e.g. Wi-Fi, WiMAX, 3G, 4G, 4G LTE, RFID, NFC), wired internet (e.g. Ethernet), USB, media card (e.g. SD, CF, xD) and displays (e.g. HDMI, VGA, DVI, DisplayPort).

The base may include an enumerator mechanism 304 which may determine the number of consumable doses (e.g. number of pills, doses of liquid) remaining in the attachable. The enumerator may be one of the following mechanisms: (1) A setup of load cells on a support platform cantilever that may weigh the cartridge and, using the known values of empty cartridge weight and single dose weight, calculate the number of single doses remaining in the cartridge; this load cell setup may perform relative measurements and automatically calibrate and correct for drift (2) a capacitance field sensing setup that may detect capacitance field across copper plates/foils embedded in opposite sides of cartridge. If attachable has its own enumerator mechanism, then the attachable's enumerator may determine the number of consumable doses instead of the base's enumerator.

The base may store one or multiple attachables in separate sockets 305 (number of sockets depends on model of base) or via one long platform/shelf that can accommodate all attachables. The base may connect to attachables via a lock-and-key or magnetic attachment (as described earlier), which may be universal across all cartridges and clips. attachable connection to base may include 5 phases (not necessarily in this order): (1) Attachable attached/placed onto base platform/socket (2) Base's enumerator mechanism determines number of doses remaining in cartridge (3) Base's reader mechanism reads and interprets digital information stored on attachable (4) Base begins to recharge battery of onboard attachable (inductively or not), if applicable (5) Audiovisual/vibrational feedback of connection process completion/attachable charging.

The base may have an integrated microcomputer, which may be an embedded Linux or other system, and may perform these functions: (1) Processing of user interface functions listed above, including but not limited to input from buttons and touchscreen(s), output to displays, user authentication, audiovisual/vibrational feedback and notifications, and entering sleep mode (2) Processing of base's reader mechanism and enumerator mechanism functions listed above, and processing of the cartridge-connection process, including but not limited to recognition/processing of attachable upon connection and performing enumerator mechanism calculations (3) Firmware update by online/USB drive/USB-to-computer (4) Download of internal memory (including but not limited to user consumption and container inventory data) to USB/wired connection devices (5) Automatically communicate/connect with cloud (via above mentioned ports) (6) Tracking and processing dispensing by user, and caching user consumption metrics/settings in internal memory and sending frequent updates to cloud (7) Performing analytics on user dispensing/consumption data (8) Resolving conflicts with redundant data on cloud (9) Sending or receipt of notifications to any device via any communication network (via ports) (10) Storage of rich user health data (including but not limited to age, gender, medical conditions) and transfer to and from cloud (11) Check for SKU recall (through cloud) (12) Communication and working in concert with any other attachables, bases and dispensers.

Dispensing Base for Advanced Attachable Management

A dispensing base may manage, dispense and/or repackage consumables from attached cartridges and loaded/empty clips (which along with other devices may be referred to as attachables), and communicate with cloud layer.

The dispensing base may have a cuboidal design or any other suitable shape, and may incorporate all or some subset of the features described herein including without limitation any combination of exterior form features, interface functions, components, systems, subsystems, processing circuitry, sensors, and so forth described herein of the base described above.

The dispensing base may include one or more attachments that may be detached and used as independent mobile devices, including but not limited to a holder, dispenser, and a manager of consumables, for example, while the user is at work or is on travel. The dispensing base may also or instead include any number of containers integrated into the base for receiving bulk dispensables in unit or continuous form so that a user can refill containers of the dispensing base as needed. The dispensing base may include an integrated dispensable delivery system such as a shared dispensing mechanism and delivery chute, which can be used by various containers and attachables, or the dispensing base may be configured operate dispensing mechanisms of various attachables for independent delivery of dispensables from each attachment, or some combination of these.

The dispensing base may include a reader mechanism configured to read digital information from attachables, as described above for the base.

The dispensing base may include an enumerator mechanism which may be configured to determine the number of consumable doses remaining in each attachable, as described above for the base.

The dispensing base may store one or multiple attachables in separate sockets 400 (number of sockets depends on model of dispensing base). The dispensing base may connect to attachables via a lock-and-key or magnetic attachment (as described earlier), which may be universal across all cartridges and clips. Attachable connection to the dispensing base may include these 5 phases (not necessarily in this order): (1) Attachable inserted and manually locked into an arrangement of support platforms (2) dispensing base's enumerator mechanism determines number of doses remaining in cartridge (3) dispensing base's reader mechanism reads and interprets digital information stored on attachable (4) dispensing base begins to recharge battery of onboard attachable (inductively or not), if applicable (5) Dispensing actuation motors are electronically activated to bring actuation arm in contact with attachable, ready for future dispensing.

The dispensing base may dispense single units or specified doses of any consumable medium, upon instruction from the user or as directed by a specific regime. Dispensing may occur through releasing single units or multiple units continuously in single unit bursts.

Dispensing via the base may bypass childproofing on attachable, so much less mechanical force may be required to dispense, potentially in the following ways: (1) Secondary attachment mechanism may connect to attachable and actuate dispensing mechanism without having to actuate the childproof mechanism (2) dispensing base socket may actuate through the action of a user loading the attachable, and may hold down the attachable's childproofing mechanism, so no further force may be required to bypass childproofing.

Dispensing output may allow for unassisted transfer of consumables from all cartridges to one common dispensing point 401 or to multiple dispensing points (e.g. one for each user, one for each consumable type, one for pills vs. liquids vs. powders); if one common dispensing point, the dispensing base may converge several chutes/tubes into one output chute/tube.

The dispensing base may be able to, upon user input, package single doses into to-go mini-packs, or chains/strips of mini-packs. Dispensing base may be able to print, in a thermographic or other manner, on each to-go mini-pack, potentially using an onboard printer.

The dispensing base may be able to heat liquids (including but not limited to water) and mix certain consumable media (including but not limited to powder-form consumables) with these liquids prior to dispensing, potentially in a liquid chamber.

The dispensing base may be able to internally manufacture consumable media (e.g. pills, liquid mixtures) from raw consumable ingredients (e.g. powders, liquids) using a variety of methods, including but not limited to pill pressing and liquid mixing.

The dispensing base may provide a simple mechanism for cleaning liquid- or powder-containing chambers/passages/nozzles.

The dispensing base may have an integrated microcomputer like the base's, which may perform all or some subset of the functions that the base's microcomputer does, as well as the following additional one: Processing and control of dispensing, packaging and compression functions listed above, including but not limited to electronic control of attachable dispensing actuation (via attachable-specific motor in socket) to release single consumable unit from specified cartridge upon user input, control of which cartridge may dispense so multiple cartridges do not dispense simultaneously, and processing of number of consumable units to dispense based on dosage, user input and recommended consumable intake.

More generally, a base as contemplated herein may be a holder, a smart base, or a dispensing base as described above, or any other device for use with dispensables as contemplated herein, and may provide any degree of integration, modularity, and functionality.

Clip for Cartridges

A clip may be a lightweight, mobile attachment to one or more cartridges, and may be fully disposable, partially disposable or fully reusable. A clip with cartridge(s) attached is referred to as a loaded clip, without cartridge attached is referred to as an empty clip.

The clip may have a welcoming and clean aesthetic design.

The clip may be powered by line power, by rechargeable internal battery (which may be recharged by base or dispenser), by AAA battery (or other size), by watch battery or by travel charger, including but not limited to an induction battery charger.

The clip may incorporate all or some subset of the audio-visual/vibrational, input, display and fingerprint/facial recognition features of the base.

The clip may incorporate all or some subset of the interface functions of the base described above (e.g. several types of digital display 500).

The clip may include a reader mechanism which may read digital information from attachables, as described above for the base. This mechanism may also or instead be a mechanical counter that increments upon successful dispensation.

Based on data from wireless access routers/towers/etc., or onboard GPS, or user input, the clip may automatically broadcast its location to the cloud layer or any base, dispenser, clip, cartridge or compatible smart device.

The clip may include an enumerator mechanism which may determine the number of consumable doses remaining in the attachable, as described above for the base.

The clip may provide an opening 501 to orient the clip to a cartridge such as any of the cartridges described above. The clip may connect to cartridge(s) via a specific lock-and-key or magnetic attachment (as described earlier). The cartridge connection to the clip may include these 4 phases (not necessarily in this order): (1) Clip attached to cartridge (2) Clip's enumerator mechanism determines number of doses remaining in cartridge (3) Clip's reader mechanism reads and interprets digital information stored on cartridge (4) Clip locking mechanism is electronically activated, ready for future authenticated dispensing.

Cartridge dispensing may include these 5 phases: (1) Before user picks up loaded clip, clip is powered down and the dispensing lock is in place (2) User picks up clip, powering device and activating fingerprint sensor (3) If authentication is enabled for this SKU/cartridge, clip processor verifies identification of user holding the device (4) Dispensing lock motor disengages (5) User can now single-dose dispense using the regular dispensing-actuation mechanism on cartridge. This process may subjectively be almost unnoticeable to the user: from picking up device to dispensing lock disengaging may take less than 1 second.

The clip may have an integrated microcomputer like the base's, which may perform all or some subset of the functions that the base's microcomputer does.

In general, the clip 500 may provide an activation and management interface for a cartridge or container of dispensables. That is, the clip 500 may house a processor, display, buttons, and so forth for autonomous operation and dispensation, thus providing enhanced functionality to a container, cartridge, or the like. The clip 500 (or a mobile base such as any of the bases described herein) may attach to a consumable container or containers and provides powered, interactive, and networked functionality such as a count of contents, an amount remaining in a container, an alert concerning a schedule for an associated user, and so forth.

Cloud Layer

Figure 32:
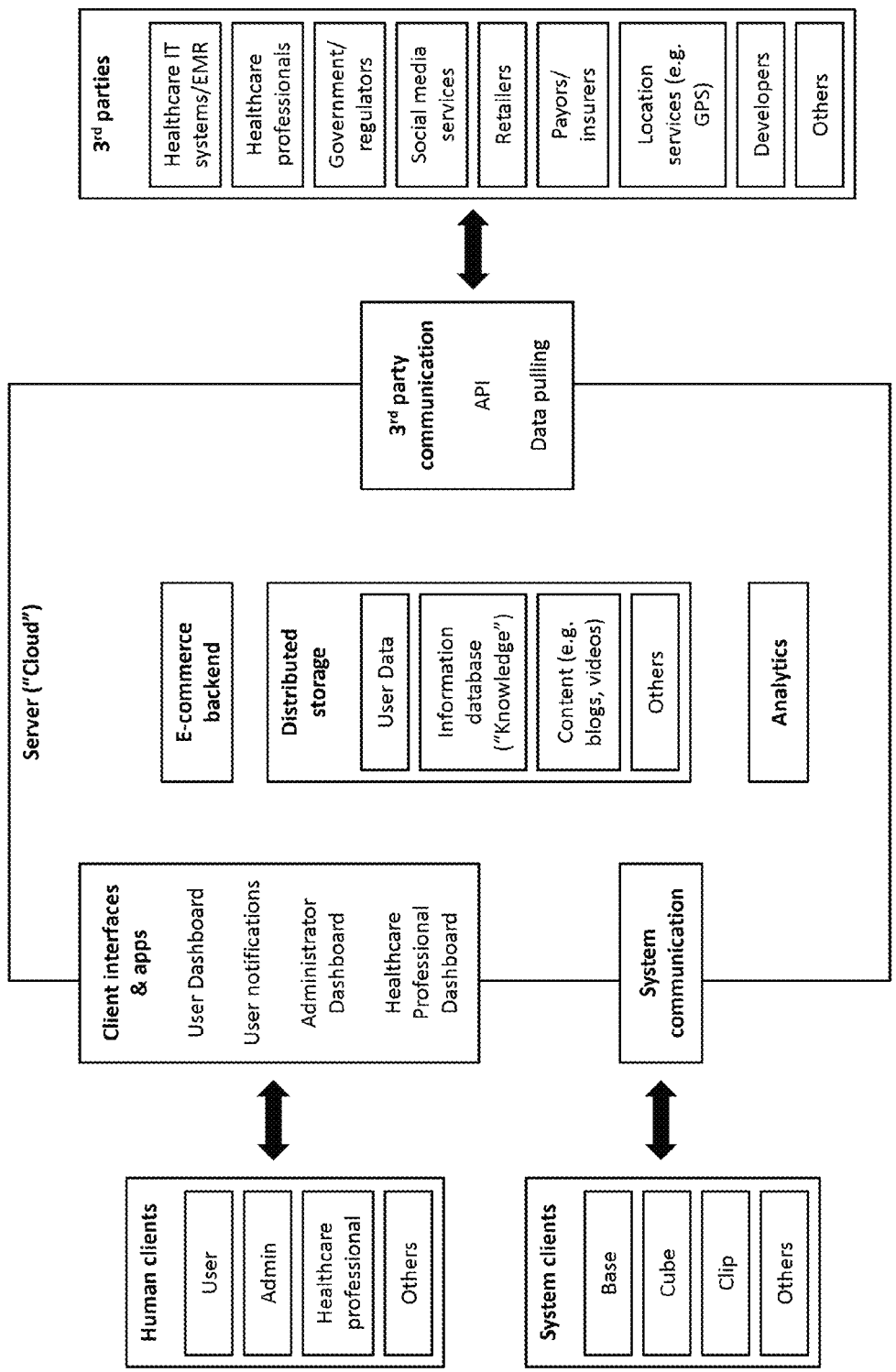
FIG. 32 illustrates cloud based functions of a system for managing dispensables.

The cloud may be a remote management system and may provide device-agnostic functionality for the disclosed system's management, usage analytics, inventory management/e-commerce and interfacing with other medical/consumer systems. Some potential features of the cloud are documented in FIG. 32.

Many features may incorporate dynamic user data which may include but is not limited to a user's preferences, personal goals, inventory, history, location, family/household and demographic data, language, financial/billing information and healthcare information (e.g. from Electronic Medical Record or insurer).

Figure 33:
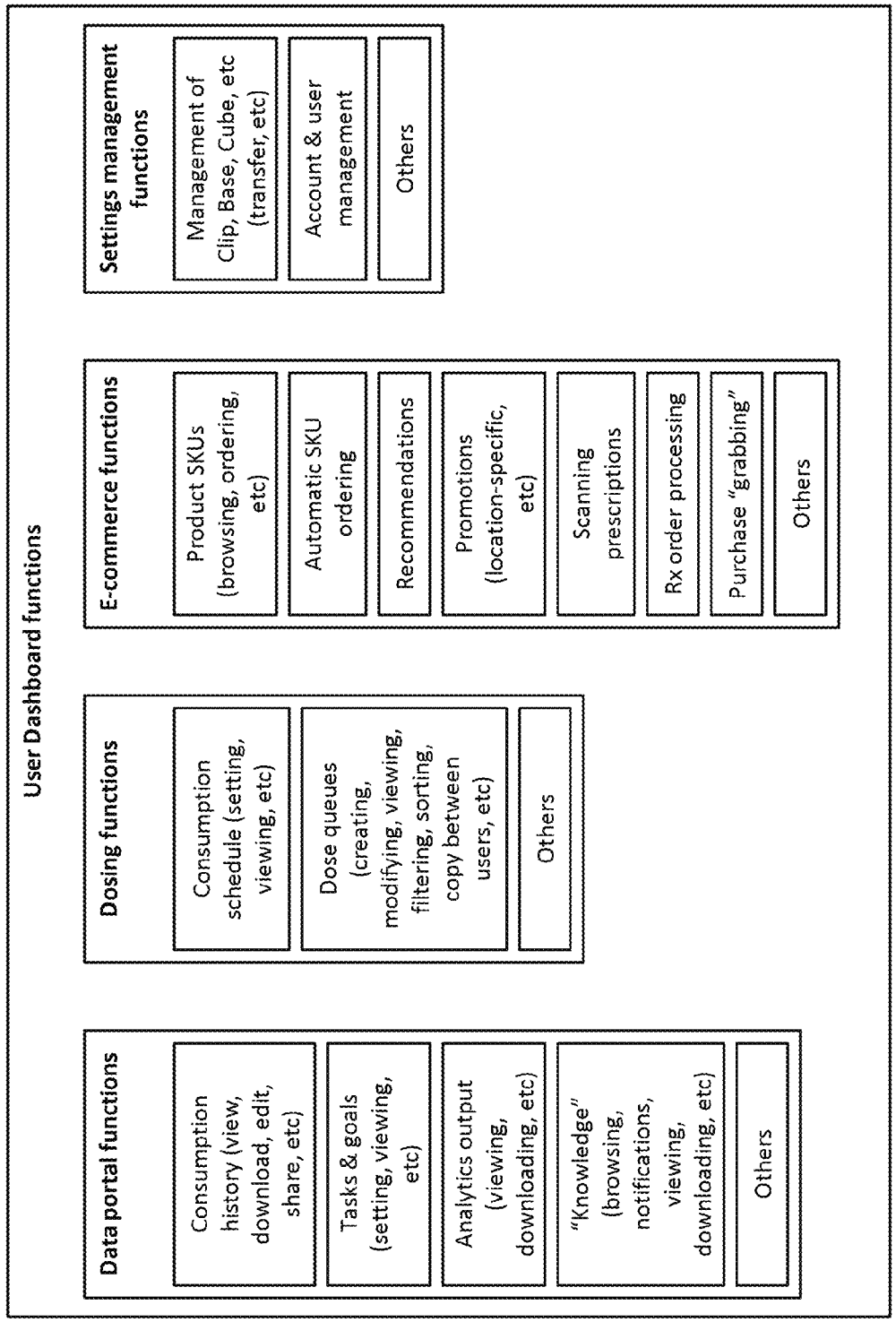
FIG. 33 illustrates functions of a user dashboard.

The device-agnostic user interface may be a user dashboard that encompasses the several user functions (data portal functions, dosing functions, e-commerce functions and settings management functions), which are all integrated into the user experience but may appear and operate separately and independently on the user dashboard. User dashboard is customized according to device it is displayed on. Some potential features of the user dashboard are documented in FIG. 33.

Data portal functions for the user dashboard may include the following: (1) Viewing, editing, downloading and sharing of user consumption history, in any format, including but not limited to CSV, PDF, XLS, XML, HTML subjectively aesthetically pleasing charts and graphs, sharing or posting onto social media portals such as Facebook and Twitter, and interface experience (also present on base and dispenser) that allows user to "drag-and-drop" images of consumable units onto images of users in account, where these images may be a default stock image or a user-uploaded image (2) Setting and viewing personal tasks (including but not limited to consumption goals and adherence goals), via means of a modifiable virtual persona or assistant, that may be monitored by cloud analytics or healthcare professionals and systems (3) Viewing and downloading analytics output, including but not limited to various healthiness metrics, personal goal progress and consumable recommendations based on user data (4) Browsing for pertinent medical information, including but not limited to drug facts, disease symptoms and treatments, physician locations and availabilities, healthcare news on medications and diseases, and site-specific content, in a manner tailored for user given user data (5) Receiving device-agnostic deliveries of this pertinent medical information, triggered by news events (e.g. drug recall, manufacturer warning letters) or user-specific events (e.g. user's family member commenced use of specific drug regimen), and tailored by user data (6) Viewing, downloading and sharing the above pertinent medical information.

Dosing functions for the user dashboard may include the following: (1) Scheduling and viewing of necessary consumption schedule for one or more users on the account, through simple drag-and-drop calendar interface (see above), tailored by user data (2) As part of scheduling, setting up manually or automatically (based on user data) a queue of doses or medicine consumption, which may be selectively shared or hidden from other users and 3rd parties (3) Sorting, filtering and viewing queues of doses by user according to consumable categorization (including but not limited to consumable indication and length of consumable's medical effects) (4) Copying, via the simple drag-and-drop interface (see above), dose queues from one user to another.

E-commerce functions for the user dashboard may include the following: (1) Browsing SKUs available online, whose displaying may be streamlined by user data (2) Placing orders for SKUs via any device, and setting automatic SKU ordering based on several trigger events, including but not limited to user inventory depletion and regular scheduled reordering (3) Receiving location-specific coupons to SKUs via user's mobile smart devices (4) Receiving personalized SKU recommendations based on user data (5) Scanning prescriptions and other paper-based medical documentation (6) Automatic uploading and order processing as soon as prescriptions are issued or scanned into system (7) Grabbing profiles of other users, in other words purchasing some or all of a specific user's historical purchase basket, if that user has shared their purchase history for grabbing purposes (8) Decision-tree based commerce.

Settings management functions for the user dashboard may include the following: (1) Management of one or multiple bases, dispensers and clips, including but not limited to remote dispensing, remote authorization of dispensing, activation of sleep mode, multi-base/dispenser/clip/cartridge management and dispensing (2) Drag-and-drop interface (see above) to copy or move settings and regimes from one base, dispenser, clip, or cartridge to another (3) Account settings management, including account setup and individual user setup (4) Disabling or enabling cloud features, to enable offline vs. cloud tracking and processing options.

Figure 34:
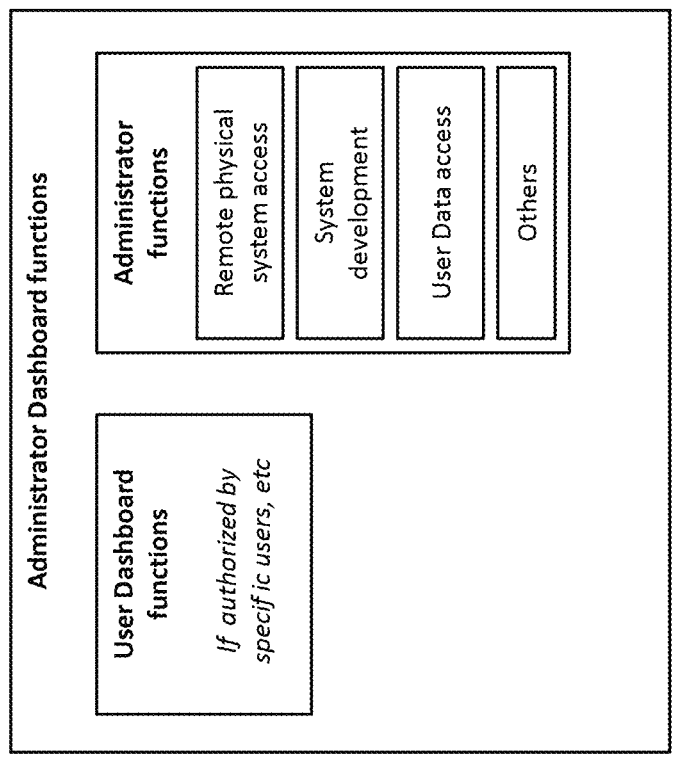
FIG. 34 shows illustrates functions of an administrator dashboard.

Administrators may include caretakers, site administrators, site developers and customer service agents. The administrator dashboard may be an interface that encompass the above user dashboard functions upon direct authorization by the user, and may additionally include the following functions: (1) Remote base/dispenser/clip access for customer service and maintenance, upon user authorization (2) Underlying system access to implement new features (3) User data and device data access, for customer service and troubleshooting, upon user authorization. Some potential features of the administrator dashboard are documented in FIG. 34.

Figure 35:
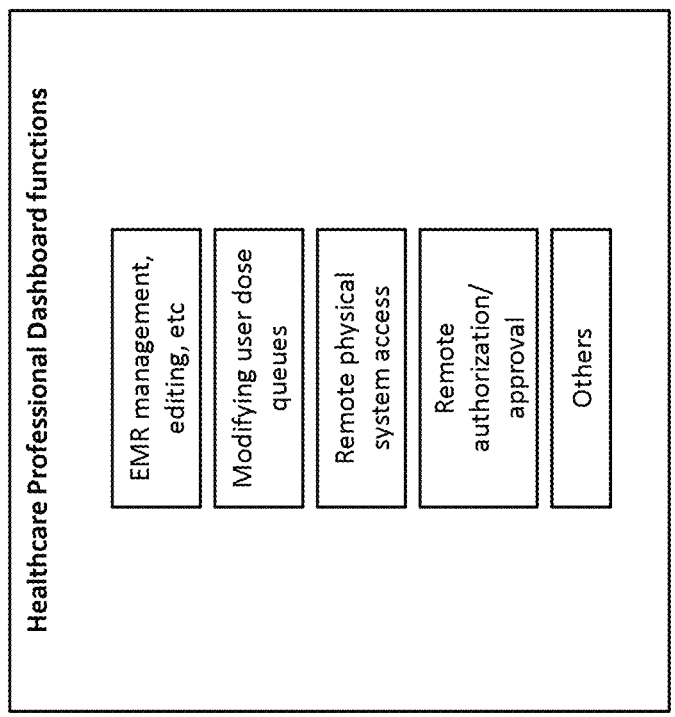
FIG. 35 illustrates functions of a healthcare professional dashboard.

Healthcare professionals may include caretakers, physicians, healthcare technicians, nutritionists and other qualified healthcare employees. The healthcare professional dashboard may be an interface that encompasses the following functions: (1) Editing a user's EMR or any other healthcare data structure, including but not limited to modifying and adding data in existing fields, and adding additional data fields (2) Inserting doses into user's dose queue or dose queues, without being able to see other doses in the dose queues, unless user provides authorization (3) Remote base/dispenser/clip access for dispensing and consumption monitoring (4) Remote authorization of pill production in base (by regulators and regulatory officials). Some potential features of the healthcare professional dashboard are documented in FIG. 35.

The cloud may perform or support two way communications with user's bases, dispensers, clips and cartridges. Further, cloud may perform two way communications with any other smart devices that a user may have (e.g. smartphone, iPad), through which the user may access the cloud interfaces. Even further, cloud may perform two way communication with medical professionals and systems (e.g. EMR systems, disease management systems, genomic/genetic platforms physicians/healthcare professionals, patient vitals tracking devices/systems and quantified-self devices/systems). Communicated data may include but is not limited to patient consumable consumption data, consumption scheduling (input by professionals or by users), medical diagnoses, directions/guidelines and prescriptions (thus user may not be required to physically visit medical authority/professional.

The cloud may download data to bases, dispensers, clips and cartridges at regular intervals or upon receiving the SKU number from those devices, e.g. SKU-specific data, firmware updates, general drug/health information and user data. The cloud may use prioritized buffering and transmission to make sure key non-redundant data is transmitted first during any communication, to ensure reliability when user devices have limited Internet access.

The cloud may deliver alert communications upon triggers including but not limited to scheduled dosing (including any dosing requirements, such as need to take drug with food), misuse (e.g. missed medication, overdose) and unsafe drug interactions (e.g. Drug A and Drug B cause stomach bleeding if consumed within 24 hrs of each other), where alerts may be in any form (e.g. emails, text messages, notifications on a base/dispenser/clip) and may travel to any device, including locally networked devices or devices within a firewall.

A particular user may have a notification state in the cloud which may escalate based on trigger events (e.g. mis-dosing); the following embodiments of notification states may exist: (Level 1:) Normal state, user may receive notifications through system devices and app notifications (Level 2:) Upon missing a dose, user may receive text messages, emails, etc. (Level 3:) Emergency state, for example upon overdosing or repeated missing of scheduled doses, user may receive phone call from human customer service agent and emergency contacts may be alerted.

All communications may be fully compliant with US and international requirements, including but not limited to HIPAA, and may be encrypted with industry standard or industry leading cryptographic technologies, such as 256-bit Rijndael encryption. All communications may pass through cloud's system servers to ensure complete reliability and security.

The cloud may connect to social media portals (e.g. Facebook) to supplement user data with additional fields, e.g. favorite foods. System may communicate with GPS towers, cells towers, Wi-Fi nodes and other wireless access points to determine or triangulate a user's location.

The cloud may connect with healthcare professionals, prescription vendors and insurers automatically upon prescription issuance or entry, potentially for order processing, drug shipment and regulatory data filing, among other functions.

The cloud may pull from multiple online databases and news sources to find and push SKU-specific up-to-date news and alerts, including but not limited to drug recalls, updated drug interactions, updated drug warnings, and manufacturer warning letters.

The cloud may require authorization from users to unlock access to cloud features as well as identify users. Methods for authorization may include but are not limited to the following: type, touch, speech, facial/visual recognition, fingerprint recognition, or combinations of these. Users may authorize certain human or automated agents to view all or a specified part of their user data. Agents may include but are not limited to doctors, hospital systems. Users may authorize agents on an individual basis or by certain agent characteristics, including but not limited to doctor specialty, doctor experience with consumable indication, and hospital group. Users may authorize site administrators and customer service representatives to access their accounts for troubleshooting and development purposes. Users that are account owners may authorize other users (whether part of their account or not) to consume certain SKUs or use certain bases, dispensers and clips.

Security of EMRs and other healthcare data structures may be enabled via data licensing and incremental digital signatures.

The cloud may provide consumable usage trend identification via an analytics engine, for (1) input to medical professionals and systems (2) warnings/recommendations based on recognized patterns and medical input (3) on demand data/visuals for users (4) modification of pricing and supply chain (e.g. contract and internal manufacturing) of consumable products.

E-commerce backend may exist for auto-replenishing of cartridges via automatically triggered orders (when Dispenser/Cases/base detect cartridges are near empty), order queuing, dose queuing and replacement of prescription filling process by connecting user with healthcare professional with prescription vendor.

The cloud may provide storage, in a distributed database, of a user's user data, base/dispenser/clip data, medical professional/system data listed above, and other data as appropriate, as well as hosting for additional content (including but not limited to blogs, user forums, site-specific media and content). User data in cloud layer may be redundant with user data on bases, dispensers and clips, and cloud performs conflict resolution as necessary. Cloud may cache frequently accessed user data for quick transmission to users and bases, dispensers and clips.

Cloud access may be provided to 3rd parties via documented API. API may allow access to evolving subset of full cloud functionality. Similarly, 3rd party APIs may be used by the system to bring 3rd party devices, networks, and ecosystems into the connected network and functionality of the dispensables system.

Customers may purchase a preset (for example "Family with children" preset) cartridge, clip, base or dispenser. For preset products, the cloud may automatically configure the vanilla product to a particular preset based on the unique product ID and the associated product purchase information from the user.

Still more generally, a variety of fixed and distributed infrastructures may be usefully employed with bases and other system components to provide value added services and augment operation of the system for an individual user. Thus portions of the systems and methods described above may be implemented in the cloud, while other portions use local processing resources for a base, such as a computer, printer, camera, and the like coupled to a local area network shared with the base or with one of the cartridges. In another aspect, other network resources may be usefully combined with cloud-based services and local processing resources to provide various layers of functionality, knowledge sharing, redundancy, and speed. For example, while a cloud-based or other remote-hosted system may manage personal inventory by automatically ordering replacement cartridges at appropriate times, this may also be performed with a suitably programmed local computer that can read compliance data, cartridge status, and scheduling information from a local base and determine when replacement cartridges might be needed. A local reminder may then be presented to the user of the base, or the computer may autonomously connect to the network and authorize or make corresponding purchases. Still more generally, a single user may wish to autonomously manage all dispensing activity, and the system may be configured as a closed system with no external network connectivity, or with limited network activity, e.g., to issue e-mail or text message alerts from the local computer. At the same time, each function described above may occur at any number of locations. For example, monitoring consumable units may be performed by a cartridge, by a clip, by a base, by a local computing device, by a dedicated remote server, or by a general purpose, cloud-based management system. Similarly various notification systems, monitoring functions, data storage functions, management and administration functions and the like may be distributed or centralized in various manners across available resources according to user preferences, security requirements, oversight required by health care professionals, data integrity requirements and so forth. All such variations are intended to fall within the scope of this disclosure, and not particular function, service, system component, sub-component, or communications interface or endpoint should be presumed to reside with any specific system element unless explicitly stated to the contrary or otherwise clear from the context.

Figure 36:
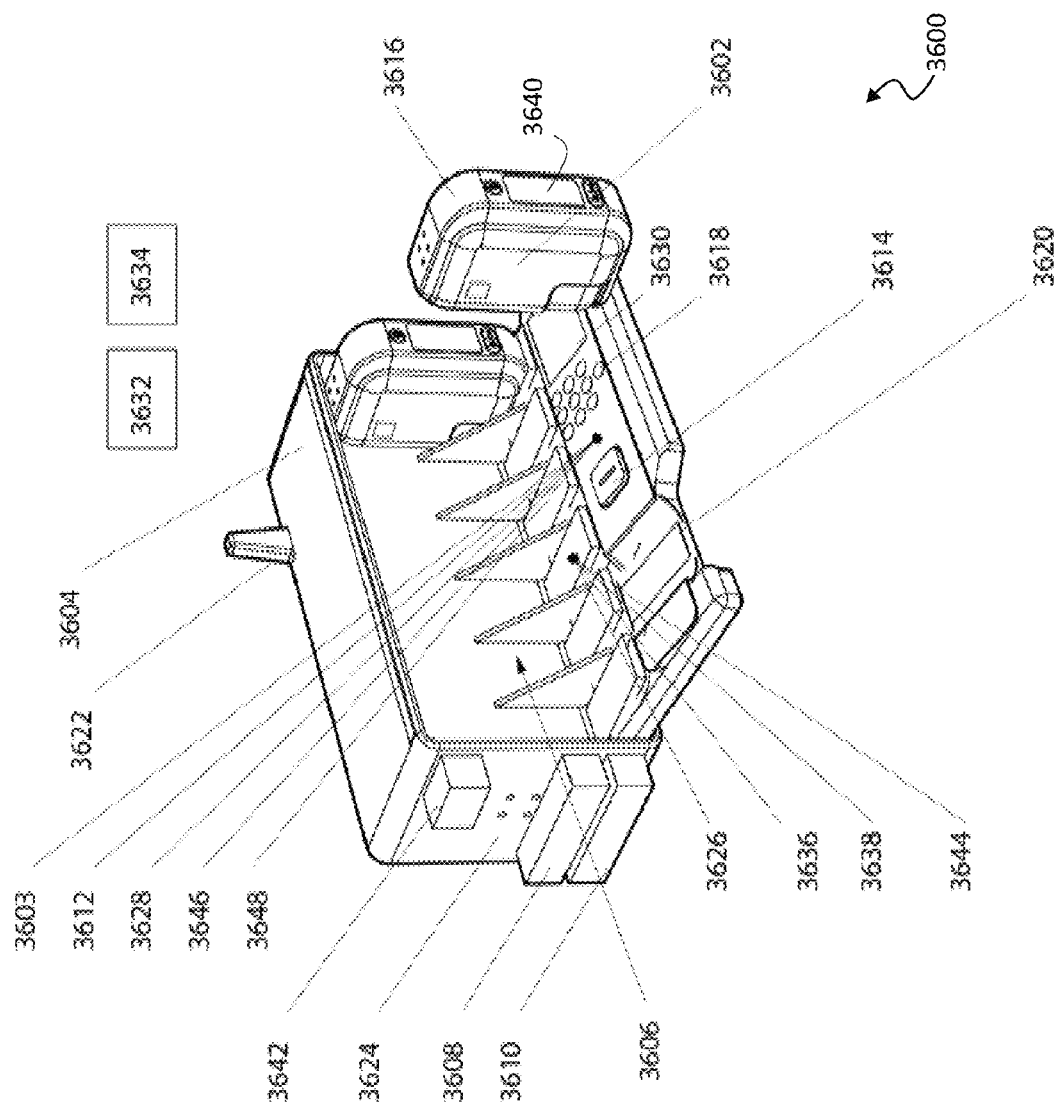
FIG. 36 illustrates a system for managing consumables for a user.

FIG. 36 illustrates a system for managing consumables for a user. In general, the system 3600 may include one or more cartridges 3602 each containing a plurality of consumable units; and a base 3604 including a processor 3603 and one or more slots 3606 to removably and replaceably receive each of the one or more cartridges, wherein the base 3604 is configured to operate each of the one or more cartridges 3602 to dispense one or more consumable units from the one or more cartridges 3602 to a user. While various components in the following description may be illustrated in specific locations, it will be understood that such components may be physically integrated into the base or one of the cartridges 3602, or externally provided as an accessory or remote resource for the foregoing, unless a different meaning is explicitly provided or otherwise clear from the context. Additionally, any components shown generally as located in the same or similar location may be located in different locations in an implementation.

Similarly, the base 3604 may be an integrated device with one or more containers for dispensables in bulk form, along with a mechanism (such as any of the mechanisms described above) to dispense individual doses of consumable units from the container(s). Where a cartridge 3602 is used that is removable from and replaceable to a base 3604, a user input such as a button or any of the other mechanisms described above, may be provided to manually activate the dispensing mechanism, and a machine input separate from the user input that is actuatable by a machine may be provided for, e.g., the base 3604 to activate the dispensing mechanism.

The base 3604 may be further configured with hardware and/or software to perform a variety of functions. For example, the base may be configured to dispense consumable units from the one or more cartridges according to a predetermined schedule stored, e.g., in a memory in the base associated with the processor.

A cartridge 3602 may contain and dispense bulk items in consumable units as described herein.

In one aspect, the base may include a compounding device 3608 to create custom dispensable from consumable units in the one or more cartridges. For example, the base 3604 may include a compounding device 3608 to create single dose of medication from the one or more consumable units. As noted above, the consumable units in each cartridge may include unit form consumables such as pills or capsules or continuous form consumable units amenable to bulk packaging such as liquids, powders, and so forth. The compounding device 3608 may include any number of active compounds to prepare dispensable from the consumable units such as a heater, a mixer, a pill press or other pill maker, an encapsulator, a spray coater, a dipping bath, and so forth. So configured, the base 3604 permits custom, on demand dispensables that meter and mix compositions from a range of different consumable units available in the one or more cartridges. In another aspect, the compounding device may be in a single cartridge 3602 that includes multiple independent dispensing reservoirs commonly controlled by the base 3604 to provide a mixed consumable in response to a single dispense instruction from the base 3604. In this aspect, the cartridge 3602 may include a mixing system to combine the two types of consumable units into a single composite consumable unit. Thus, the compounding device 3608 is broadly applicable to any of the dispensers in the system (e.g., cartridge or base).

A packaging mechanism may be incorporated into the compounding device 3608, or provided instead of or in addition to the compounding device 3608, to wrap one or more dispensed consumables in a disposable packaging such as a paper wrap, blister pack, or the like. In this manner, consumables can be dispensed in packaging for convenient transportation.

The base may include a printer 3610 such as a thermal printer, laser printer, inkjet printer, contact printer, or the like for labeling and other functions. In one aspect, the processor of the base may be configured to print dosing instructions for consumable units in one of the cartridges with the printer. The printer may print dosing instructions on an adhesive strip shaped and sized to attach to one of the cartridges so that a cartridge can be removed from the base and carried with readily available dosing instructions similar to a conventional pill bottle or the like. In another aspect, the processor may be configured to dispense a plurality of consumable units for a predetermined time interval according to a predetermined schedule, and wherein the processor is further configured to print dosing instructions for the plurality of consumable units within the predetermined time interval. In this manner, a user may print a time-specific itinerary or dosing schedule and dispense corresponding consumable units so that, for example, consumable units and corresponding dosing information can be carried by a user without any need to rely on the base or cartridges for the predetermined time interval (e.g., several days for travel, or the like). The packaging system may be concurrently used to provide temporary, disposable packaging for the consumable units in this temporary, portable schedule. In another aspect, the consumable units may include one or more pills and one or more sachets in bulk form, and the base may be configured to package one of the one or more pills in one of the one or more sachets, thereby providing a packaged item, and to dispense the packaged item from the base. In this context, the printer may be configured to print individual dosing instructions the packaged item before it is dispensed by the base. The predetermined schedule may be a prescription schedule administered by a health care professional.

In general, the consumable units may include but are not limited to medications. For non-prescription medications or the like, the predetermined schedule may be a user-created dosing schedule or regimen. The plurality of consumable units may also or instead include a nutritional supplement. The plurality of consumable units may also or instead include one or more of an over-the-counter medication, a vitamin supplement, a mineral supplement, a prescription medication, a veterinary medication, and a veterinary nutritional supplement.

The system may include a social networking platform 3612 which may interact with the base and/or a user in a variety of ways. The platform may be configured to share the user-created dosing schedule with one or more other users. The platform may be configured to facilitate a modification to another dosing schedule for another user, including but not limited to consumers, administrators, caretakers, and healthcare professionals. The platform may be configured to forward a recommendation for a dosing schedule to another user. The platform may be configured to receive a second dosing schedule from another user. The platform may be configured to facilitate a modification to the dosing schedule according to a second dosing schedule of another user. The platform may be configured to receive a recommendation for a modification to the dosing schedule from another user.

The predetermined schedule or regimen may serve a variety of functions and take a variety of forms generally related to timing of delivery of consumable items in the one or more cartridges. This may generally include personally configured schedules, professionally configured schedules, or combinations of these. For example, the predetermined schedule includes a first schedule provided by a health care professional for one or more medications and a second schedule provided by the user for one or more nutritional supplements. The predetermined schedule may include two or more schedules from two or more entities. The predetermined schedule may include dosing of the consumable units from two or more of the cartridges substantially concurrently. The predetermined schedule may include specific times for the user to take the consumable units. The base may store dosing information with the predetermined schedule, such as information about a medium to be combined with one of the consumable units prior to consumption (e.g., mix with one cup of water) or a medium to be ingested with one of the consumable units (e.g., take two with each meal). The predetermined schedule may include relative times for the user to take the consumable units. The relative times may include a time relative to one or more of a sleep event, a wake up event, an activity, a travel event, an indication-specific event, and a meal event. Thus for example, the schedule may indicate a dose-related event (e.g., take before physical activity) without requiring a dose at any predetermined time. This may be coupled with an input device for the base with which a user can indicate an occurrence or imminent occurrence of the dose-related event in order to receive corresponding, scheduled consumable units. Thus, the base may include an input device 3614 to receive a user indication that an event associated with the relative time has occurred (or for any other user input). The input device may include a button, a touch screen, or any other suitable input device. The predetermined scheduled may include dosing for two or more users. The base may be configured to manually dispense one of the consumable units from one of the cartridges in response to a user input, and to update the predetermined schedule according to a corresponding dosage.

One of the cartridges may include a clip 3616 that is separable from the cartridge. The clip may be shaped and sized to hold the cartridge and to fit in to one of the slots of the base. Thus it will be understood that the "cartridge" as contemplated herein may in certain circumstances include the clip, such as where the clip is required to fit the cartridge into one of the slots, or the cartridge may be a separate device from the clip, such as where describing various allocations of functionality and features between the clip and the cartridge, many combinations of which are possible. It will be thus understood that the clip is not necessarily separate from or included in the cartridge, and the appropriate meaning will in general be expressly stated or clear from the context. In one aspect, the clip may electrically couple the base to the one of the cartridges in a communicating relationship. In another aspect, the clip may mechanically couple the base to the one of the cartridges in order to mechanically, electrically, or otherwise dispense one of the consumable units from the one of the cartridges. The clip may include a processor configured to control operation of the cartridge. The system may also include a plurality of clips and a plurality of cartridges, each one of the plurality of clips removably and replaceably attachable to each one of the plurality of cartridges.

The base may include a user interface device 3618 or system for a variety of functions related to user interactions. For example, the base may include a keypad configured for passcode authentication of the user. The base may include a voice recognition user interface for user interaction with the base. The base may include a gesture recognition system for user interaction with the base. The base may include a voice recognition system for authenticating the user. The base may also or instead include voice recognition or speech recognition to support an interactive voice response interface for spoken interactions with a user. The base may include a facial recognition system for authenticating the user. The base may include a biometric system for authenticating the user. The biometric system may include a fingerprint identification system or any other biometrically based identification system using, e.g., eye recognition or any other suitable recognition technique. The base may be configured to authenticate the user before dispensing the one or more consumable units.

The base may include one or more chutes 3620 positioned to receive the consumable units from one or more cartridges and guide the consumable units to a user-accessible location. The user-accessible location may include a sensor to detect when the one or more consumable units have been removed by the user. In one embodiment, multiple bases could function as modules and attach to each other, in a manner that, for example, connects their chutes 3620 together into one or more integrated chutes.

The system may include an output device 3622 to transmit notifications from the base, or to transmit notifications about a predetermined schedule from some other location such as a management server, local computer, or the like. In this manner, the base may be configured to notify the user with the output device when one or more consumable units have been dispensed. The output device may include one or more of a buzzer, a speaker, a display, and a light-emitting diode. The output device may include a network communications device configured to transmit at least one of a text message, an electronic mail, and a telephone message. The output device may notify a health care system when the one or more consumable units are dispensed, such as for compliance monitoring or the like. The output device may transmit a user-configured notification to a user-selected entity when the one or more consumable units are dispensed. The output device may include a push notification system for pushing notifications to one or more of a mobile device and a remote application.

More generally, the system may include a notification system 3624, which may be present on the base station, a remote server, a local computer, a portable computing device of the user, or any other location or combination of locations, to alert the user of a dosage in the predetermined schedule, or to more generally provide notifications to the user or third parties upon any predetermined conditions. The notification system transmit may be configured to provide a series of escalating alerts for increasingly urgent reminders about doses in the predetermined schedule. For example, a first alert may be transmitted to the user when the dosage is due. The notification system may conditionally transmit a second alert to the user when the dosage is be missed by the user. The notification system may conditionally transmit a third alert to the user when the user does not respond to the second alert for a predetermined time, wherein the third alert may include a notification to a call center to contact the user. The third alert may be transmitted to one or more health care professionals. More generally, the notification system may be a user-configurable notification system. The notification system may be configurable to provide a sequence of escalating notifications using a number of communication mediums according to deviations from the predetermined schedule. The notification system may be configurable by a third party to provide one or more notifications according to deviations from the predetermined schedule. Thus for example, a health care professional, concerned relative, or other authorized user may remotely manage medication or the like administered by the base through automated notifications generated by the notification system. The third alert may be transmitted to one or more predetermined contacts for the user.

One or more of the cartridges may include a communications interface 3626 to the base station and circuitry configured to communicate a numeric count of the plurality of consumable units in the cartridge to the base station through the communications interface. The communications interface may include a wireless interface. The wireless interface may include a radio-frequency identifier (RFID) tag interface. The wireless interface may include a near field communications interface. The wireless interface may include one or more of a Bluetooth interface, a Wi-Fi interface, a ZigBee interface, a Z-Wave interface, an Insteon interface, an EnOcean interface, a DECT interface, and an infrared interface. This interface may allow connection to or formation of a network, including but not limited to a local area network, an ad-hoc network, an open mesh, and a peer-to-peer network.

One of the cartridges may include a memory configured to store the numeric count of the number of consumable units in the cartridge. The cartridge may include circuitry configured to detect the numeric count of the number of consumable units. The system may include an order fulfillment system 3628. The base may be configured to dispense consumable units from the one or more cartridges according to a predetermined schedule, and the order fulfillment system may compare the numeric count of the plurality of consumable units to the predetermined schedule to determine when a replacement cartridge should be ordered for the user. The order fulfillment system may include computer code executing on the processor of the base. The order fulfillment system may also or instead include computer code executing on a remote server coupled in a communicating relationship through a data network to the base. The order fulfillment system may be configured to order the replacement cartridge. The order fulfillment system may be configured to notify the user to order the replacement cartridge.

The system may include a management interface 3630 to provide a variety of management functions associated with dispensing consumable units from the base and related user health and wellness issues. The management interface may include a graphical user interface for managing the predetermined schedule. The management interface may be hosted on a remote server coupled in a communicating relationship with the base. The management interface may include a web interface configured for remote access. The management interface may be hosted on the base. The management interface may include a web interface configured for remote access. The management interface may be provided by an application executing on a computing device such as a laptop, desktop, tablet, smartphone or other device. In general, the computing device may be wirelessly coupled to the base through a local area network. The computing device may be coupled to the base through a wired connection. The wired connection may include one or more of a wired Ethernet connection, a USB connection, a FireWire connection, a Lightning port, a Thunderbolt interface, an eSATA interface, an HDMI interface, a CAN bus interface, an ExpressCard interface, a Fieldbus interface, a Futurebus interface, a DisplayPort interface, a UPB interface, an X10 interface, and a PCI Express interface.

The management interface may be configured for the user to modify the predetermined schedule. The management interface may be configured to limit modifications to the predetermined schedule to one or more authenticated individuals. The management interface may be configured to limit modifications to the predetermined schedule to one or more qualified health care professionals. The management interface may be configured to display compliance information. The management interface provides a drag-and-drop interface to transfer the predetermined schedule from one base to another base. The management interface may provide a drag-and-drop interface to transfer the predetermined schedule for a particular type of consumable unit from one cartridge to another cartridge. The management interface may provide a drag-and-drop interface for removing an association of one of one or more cartridges with the base. The management interface may provide a drag-and-drop interface to allocate a consumption of the consumable units in one of the cartridges to the user. The management interface may provide a drag-and-drop interface to allocate a type of consumable unit to the user.

In another aspect, the system may include a remote management system 3632 coupled in a communicating relationship with the base. The remote management system may identify a low level in one of the one or more cartridges. The remote management system may determine whether a prescription for the user may include additional dosages for a type of medication in the one of the one or more cartridges, thereby providing a prescription verification. The remote management system may initiate a managed care billing request for a replacement cartridge based upon the prescription verification. The remote management system may initiate a payment from the user based upon the prescription verification. The remote management system may initiate an order for the replacement cartridge with a vendor. The remote management system may provide an auction platform configured to receive a pre-authorization from the user to purchase a replacement cartridge for the one of the one or more cartridges, and to process bids from one or more vendors to fulfill an order for the one of the one or more cartridges. The remote management system may provide a reseller market for sale of used cartridges. The remote management system may provide a virtual market for one or more of the one or more cartridges. The remote management system may determine a purchasing history for the user and initiates a purchase of one or more replacement cartridges for the user based upon the purchasing history. The remote management system may monitor compliance for the user according to one or more prescriptions from one or more health care providers. The remote management system may provide a compliance report to one or more third parties. The one or more third parties may include at least one health care provider. The remote management system may compare one or more prescriptions from one or more health care providers to ensure compatibility of the one or more prescriptions.

Where the base is configured to dispense consumable units from the one or more cartridges according to a predetermined schedule, the remote management system may compare one or more consumable units in the predetermined schedule for drug interactions based on data from one or more of warning databases, government sources, drug label information, pharmaceutical companies, healthcare groups, health care providers, and patient groups. The remote management system may monitor consumable units dispensed from all of the cartridges registered with the base to the user to determine an actual medication regime for the user, and the remote management system may check for counter-indications within the actual medication regime. The remote management system may be further configured to generate an alert to one or more health care providers for a counter-indication identified within the actual medication regime. The remote management system may be further configured to generate an alert to one or more predetermined contacts for a counter-indication identified within the actual medication regime. The base may be configured to dispense consumable units from the one or more cartridges according to a predetermined schedule, and the remote management system may detect one or more consumable units manually dispensed from the base and update the predetermined schedule on the base.

The system may include a financial processing system 3634 for processing various financial transactions associated with use of the base and/or cartridges. The financial processing system may be coupled in a communicating relationship with the base through a data network such as the Internet. The financial processing system may be configured to initiate a payment authorization from the user for a replacement cartridge. The replacement cartridge may be identified from a recurring schedule of replacements. The financial processing system may be configured to initiate a payment authorization from a health insurance provider for the replacement cartridge. The financial processing system may be configured to initiate a payment authorization from a third party payor for the replacement cartridge. The financial processing system may be configured to initiate a payment authorization from a health insurance provider for a recurring charge to use the base. The financial processing system may be configured to initiate a payment to a provider of a replacement cartridge.

The base may include other hardware 3636 such as a variety of input devices, output devices, sensors, communications devices, and so forth. For example, the base may include a radio-frequency identification tag reader configured to retrieve data from one of the one or more cartridges. The base may include a local area network interface. The local area network interface may be a short range wireless interface configured to couple the base station in a communicating relationship with a computing device of the user. The short range wireless interface may include a Wi-Fi network interface. The base may include a network interface to couple the base in a communicating relationship with a remote resource using a data network such as the Internet. The base may be configured to communicate through the network interface with one or more of the remote management system, the financial processing system, and the order fulfillment system described above. The base may be configured to communicate through the network interface with one or more of a health care provider system, a health insurance provider system, a retailer, and a pharmacy. The base may include a cellular network interface. The base may be configured to couple in a communicating relationship with a remote resource through the cellular network interface. The cellular network interface may include one or more of a 3G interface, a 4G interface, and an LTE interface.

The system may include an interface 3638, such as any of a number of mechanical, electrical, and/or electromechanical interfaces between the base and one of the cartridges. For example, each of the one or more slots may include a locking mechanism to mechanically secure one of the cartridges in the one of the slots. The locking mechanism for one of the slots may be configured to automatically lock upon insertion of one of the cartridges into the one of the slots. The base may include a user-activated release to unlock one of the locking mechanisms for removal of a corresponding one of the cartridges. The user-activated release may be a mechanical release. The user-activated release may be an electro-mechanical release. Each of the one or more slots may include one or more mechanical registration features to receive one of the cartridges in a predetermined orientation. Each of the one or more slots may include an electronic interface to electrically couple the base to one of the cartridges. The electronic interface may include a power coupling, the base further configured to provide power to the one of the cartridges through the power coupling. The electronic interface may include a data interface, the base further configured to exchange data with the one of the cartridges through the data interface. The base may include a wireless power delivery system configured to wirelessly provide power to at least one of the cartridges. The system may include a childproofing mechanism on at least one of the one or more cartridges such as a keycode for authorized access or a mechanical lever, button, or the like that increases the difficulty for a child to access the consumable units in the cartridge. The system may include a bypass mechanism on the base to bypass the childproofing mechanism. The bypass mechanism may include a user authentication system in the base. The clip may include a bypass mechanism to bypass the childproofing mechanism.

Each of the one or more cartridges may include a unique identifier 3640. The unique identifier may be optically encoded on each of the one or more cartridges. The base may include an optical scanner for reading the unique identifier. The base may include one optical scanner 3642 for each one of the slots, wherein the unique identifier may be positioned in a predetermined location on each one of the one or more cartridges and wherein each optical scanner may be positioned to capture an image of one of the unique identifiers when one of the cartridges may be placed in a corresponding one of the slots.

The system may include a weight sensor 3644 configured to detect a weight of contents of one of the one or more cartridges. The system may include processing circuitry configured to calculate a consumable unit count for the one of the one or more cartridges based upon the weight. The system may include calibration circuitry configured to adjust the consumable units count according to one or more of temperature, humidity, time and desiccant activity. The weight sensor may be in the base, or the weight sensor may be in one of the cartridges, or the weight sensor may be distributed between these components.

The system may include a central repository 3646 such as a data store, remotely accessible database, or the like accessible through the data network for checking one of the cartridges against external data sources including one or more of user data, healthcare databases, official news sources, unofficial news sources, government news sources, and alert services. In this manner, the contents of a cartridge may be checked at a SKU level for recalls, warnings, counter-indications, and so forth based on the specific contents of the cartridge and the most recent information available. The central repository may provide data for checking the plurality of consumable units in the one of the cartridges against external data sources.

The system may include a goal setting platform 3648 to assist a user in achieving a goal in cooperation with contents of the cartridges and a schedule for consumable units. The goal setting platform may be configured to receive a goal of a user and provide reminders to the user related to the plurality of consumable units in the one or more cartridges. The goal setting platform may also or instead be configured to provide reminders related to the goal and unrelated to the plurality of consumables.

The system may include cartridge data for one of the cartridges stored in a cartridge memory, along with a remote data store that redundantly stores the cartridge data. The cartridge memory may reside in the base, or in one of the cartridges. A reconciliation service may be provided to reconcile data between the remote data store and the cartridge memory.

The system may include a network interface for coupling one of the cartridges to the data network, with the network interface configured to transmit data between the cartridge and a remote resource according to a priority. In this manner, data may be prioritized, such as in limited connectivity contexts, to ensure that the most important or highest priority data is exchanged first. The priority may be based on a degree of redundancy so the least redundant data is exchanged first. The prioritization may occur at any point in the corresponding data connection, and may for example be implemented in one or more of the cartridge, the base, and the remote resource. In one aspect, the network interface may include a wireless communication interface in the one of the cartridges, which may couple in a communicating relationship to, e.g., the base station with a short range wireless protocol or a wide area data network using a cellular or other wireless data network infrastructure.

One of the cartridges may include two types of consumable units in two independently dispensing reservoirs. More generally, one of the cartridges or any number of the cartridges may include three or more types of consumable in three or more independently dispensing reservoirs. The independently dispensing reservoirs may be independently controllable by the base in order to permit customized consumable units based on mixtures of the two or more types of consumables. The two independently dispensing reservoirs may also or instead be commonly controlled by the base to provide a mixed consumable having a predetermined composition in response to a single dispense instruction from the base. The cartridge may also include a mixing system such as a stirring system, blending system, agitation system, pill press, and the like to combine the two types of consumable units into a single, composite consumable unit, which may be a pill, a capsule, a suspension, and a solution. In this manner, a cartridge may serve as a personal compounding system for home-made medications, supplements, and so forth.

Figure 37:
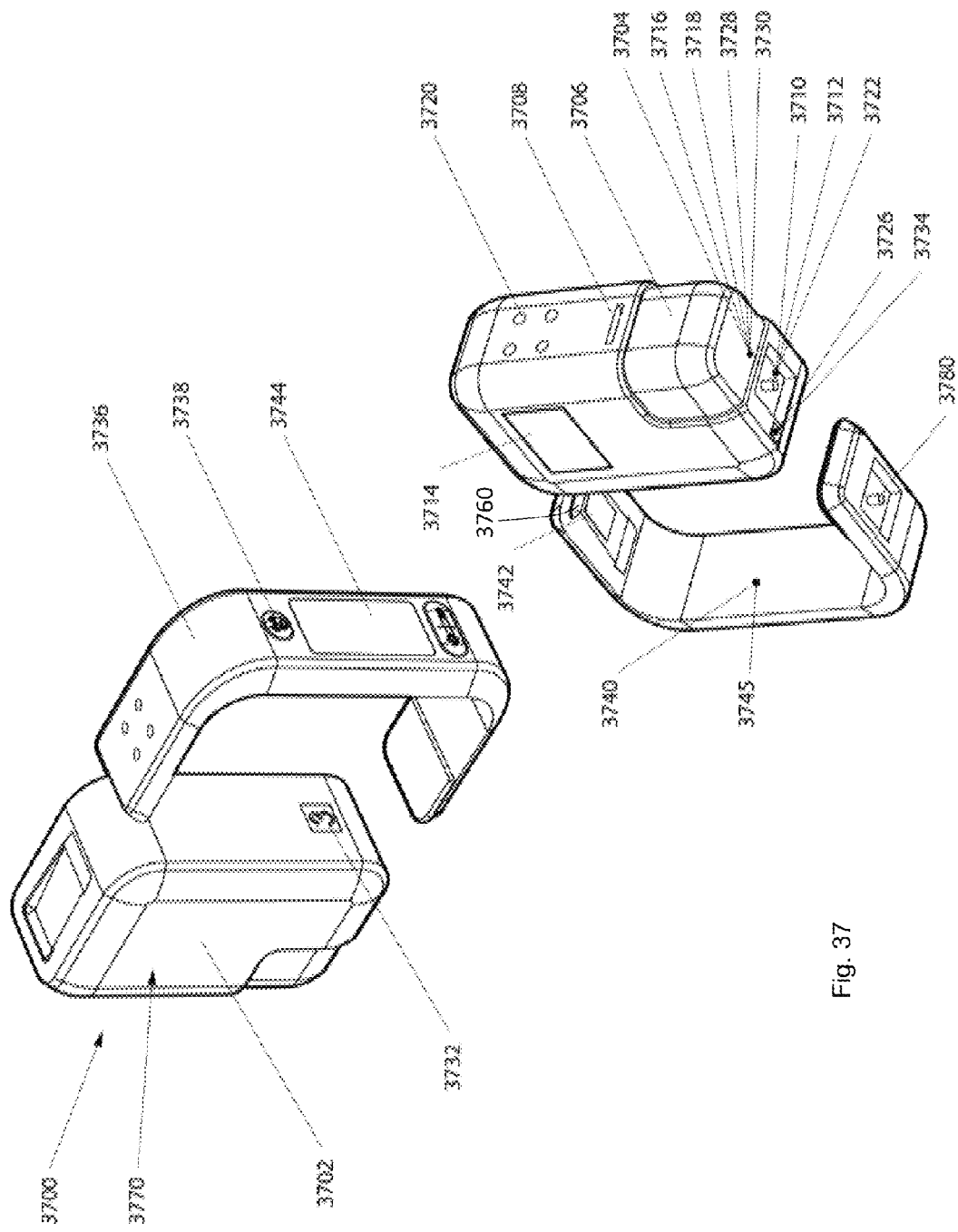
FIG. 37 illustrates different views of a cartridge and clip.

FIG. 37 illustrates different views, a rear perspective view and a front perspective view, of a cartridge and clip. In one aspect there is disclosed herein a device 3700 (optionally with or without the clip) that includes a container 3702 configured to hold a plurality of consumable units; a mechanism 3704 to dispense individual doses of the plurality of consumable units from the container; a user input 3706 to manually activate the mechanism and dispense one of the plurality of consumable units; a machine input 3708 to activate the mechanism and dispense one of the plurality of consumable units, e.g., in response to a signal from a base (when the device 3700 is coupled to a base); and a mechanical interface 3710 including one or more mechanical registration features to removably and replaceably insert the device into a base. In general, the one or more registration features align the device to the base in a predetermined alignment.

The device may include a locking mechanism 3712 to securely retain the device in the predetermined alignment in the base, which may be disposed on the device, on the base, or between the two. The device may include a battery 3714 or other power source to provide power to the device for electronic operation. The device may include a processor 3716. The device may include a memory 3718 configured to store a predetermined schedule for delivery of the plurality of consumable units to a user. The device may include an output device 3720 to notify the user of a time to take one of the plurality of consumable units according to the predetermined schedule.

The device may include an electronic interface 3722 adapted to electrically couple the device to the base when the device may be in the predetermined alignment. The electronic interface may be a power interface. The electronic interface may be a data interface.

The device may include a radio-frequency identification tag 3726.

The device may include communications circuitry 3728 for one of more of near field communications, Bluetooth communications, ZigBee communications, Z-Wave communications, Insteon communications, EnOcean communications, and DECT communications. The device may include communications circuitry for one or more of CDMA communications, 3G communications, 4G communications, LTE communications, and WiMAX communications. The communications circuitry 3728 may also or instead include a network communications device (such as a wired or wireless Ethernet or other 802.xx device) configured to notify a user to take one of the consumables in the container 3702 according to the schedule. The communications device may transmit a notification using at least one of a text message, and electronic mail, a VoIP message, a push notification to a mobile device application, a telephone message, and the like, and/or a signal to a remote notification platform to similarly transmit a notification using any of the foregoing.

The user input may manually activate the machine input. The memory may be configured to store a numeric amount of the plurality of consumable units in the container. The device may include one or more sensors 3730 to detect the numeric amount. The device may include processing circuitry to update the numeric amount when one of the plurality of consumable units may be dispensed from the container. The device may include a mechanical counter 3732 to indicate a numeric amount of the plurality of consumable units in the container.

The mechanism may include an agitator and a chute, the agitator responsive to the user input or the machine input to agitate the number of consumable units in the container, thereby dispensing one of the plurality of consumable units through the chute. The chute may be an asymmetrical chute. The agitator may be an asymmetrical vertical agitator or asymmetrical horizontal agitator.

The device may include a machine-readable identifier 3734. The machine-readable identifier may uniquely identify the device. The machine-readable identifier may encode information about the device. The machine-readable identifier may encode information about contents of the container of the device. The machine-readable identifier may encode an expiration date for a consumable unit associated with the contents of the container. The machine-readable identifier may encode a Stock-Keeping Unit (SKU) for the contents of the container. The machine-readable identifier may encode one or more of a name for the SKU, a milligrams-per-dose of SKU consumables, a weight of empty cartridge for the SKU, a weight of a single unit of SKU consumables, a warning for the SKU, and directions and guidance for the SKU. The machine-readable identifier may include a radio-frequency identification tag. The machine-readable identifier may include a Quick Response code. The machine-readable identifier may include a bar code.

The device may include a clip 3736, which may be removably and replaceably coupled to the device. The clip may provide the mechanical interface for coupling to the base. The clip may connect to the mechanical interface of the device. The clip may include a user-operable button 3738 configured to activate the machine interface of the device. Thus in one aspect, the clip 3736 may include a first mechanical interface 3760 configured to removably and replaceably couple to a container 3702, which as shown may be housed in a cartridge 3770 providing various other components for various features and functions. The clip 3736 may also include a second mechanical interface 3780 configured to removably and replaceably couple to a base such as any of the bases described herein. In general, this clip 3736 may serve as an intermediate component supporting communication interfaces between the cartridge 3770 and the base (not shown) and permitting an exchange of information therebetween. The clip 3736 may also store information such as a schedule (from the base) and a quantity of consumables (from the cartridge 3770) to facilitate removal of the clip/cartridge combination from the base for temporary independent use.

The clip may include a memory 3740 storing a numeric amount of the plurality of consumable units in the container. The clip may be configured to obtain the numeric amount from the device. The clip may be configured to obtain the numeric amount from the base. The clip may update the numeric amount when one of the consumable units is dispensed from the device. The memory may also or instead store a predetermined schedule for delivery of the plurality of consumable units to a user. The clip may include an output device 3744 to notify the user of a time to take one of the plurality of consumable units according to the predetermined schedule.

The clip may include a power source 3742. The power source may be configured to provide power from the power source to the device. The clip may be configured to communicate data between the device and the base. The clip may include a display 3744 to display a numeric amount of the plurality of consumable units in the container of the device.

The clip may be configured to hold a plurality of devices. The clip may be configured independently control each one of the plurality of devices.

In one aspect, the device may include a memory configured to store a predetermined schedule for delivery of the plurality of consumable units to a user and a processor 3745 may be configured to couple the device in a communicating relationship with the base when the device may be inserted into the base. The processor may be configured to retrieve an update to the predetermined schedule from the base and/or the processor may be configured to transmit consumable unit delivery data for the container to the base.

As noted above, the device may include a clip coupled to the device that provides the mechanical interface for insertion into the base, the clip may include a processor, a first communication interface to communicate with the base, and a second communication interface to communicate with the device. In this configuration, the processor may be configured to couple the device in a communicating relationship with the base. The clip may be configured to provide an updated predetermined schedule from the base to the device when the clip and the device are inserted into the base in the predetermined alignment. The clip may be configured to provide consumable unit delivery data for the container to the base when the clip and the device are inserted into the base in the predetermined alignment.

Figure 38:
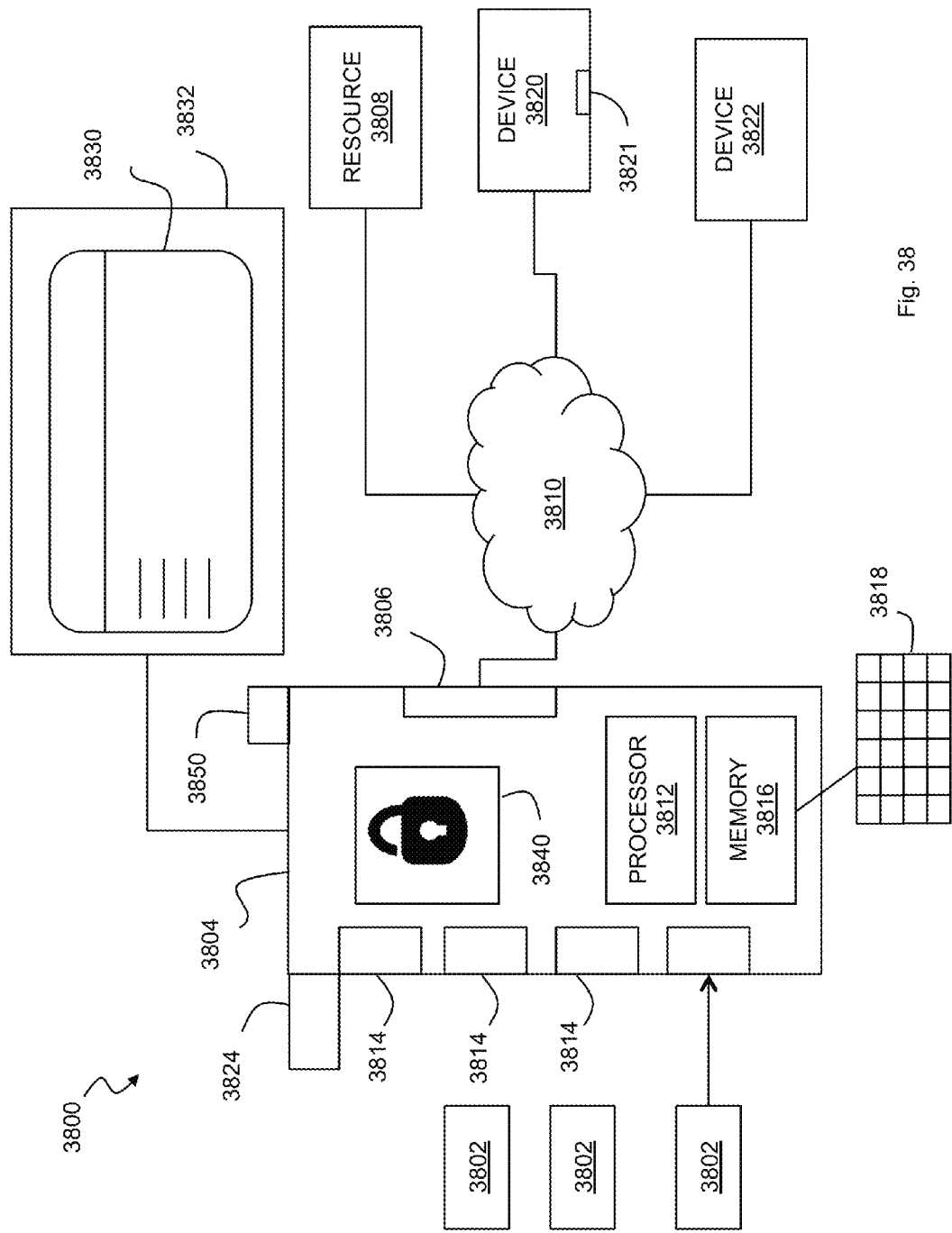
FIG. 38 shows a system for managing consumables.

FIG. 38 shows a system for managing consumables. In general, the system 3800 may include one or more containers 3802, a base 3804, and a network interface 3806 to couple the base 3804 in a communicating relationship with a remote resource 3808 through a data network 3810. The base 3804 may include a processor 3812 and one or more slots 3814 to removably and replaceably receive the containers 3802.

Each of the containers 3802 may contain a plurality of consumable units as generally contemplated herein. While the following description focuses on consumable units, it will be understood that the containers 3802 may contain any of the dispensables described herein. It should also be understood that, without loss of generality, the systems described herein may also be implemented with "containers" that are formed by bins or the like integrated directly into the base 3804, so that removable and replaceable containers are not required and consumables are provided by a user directly to the bins in bulk form.

In one aspect, one of the containers 3802 may include a communications interface to communicate with the base and circuitry configured to communicate a numeric count of consumable units in the container 3802 through the communications interface. The container 3802 may also or instead communicate any useful property of the consumable units in the container such as weight, expiration date, and so forth.

The base 3804 may include a processor 3812 configured to operate each of the containers 3802 (when positioned in the slots 3814) to dispense consumable units. As described above, this may include operating each container 3802 to individually dispense consumable units, such as into a common chute provided by the base 3804 or from a chute specific to the corresponding container 3802, or this may include operating the base 3804 to retrieve consumable units from each container 3802, or some combination of these. The base 3804 may include a memory 3816 storing a schedule 3818, which may be any of the schedules described herein. The memory 3816 storing the schedule 3818 may also or instead be in one or more containers 3802, or in the remote resource 3806, or distributed among these components. In general, the processor 3812 may be configured to receive changes to the schedule from a first remote device 3820 through the data network 3810, and to transmit information about the containers 3822 to a second remote device 3822, which may be the same device as the first remote device 3820 or a different device.

In one aspect, the base 3804 (e.g., with the processor 3812) may be configured to provide a notification to a user of an item on the schedule 3818. The base 3804 may also automatically dispense a corresponding consumable (which may occur with or without notification to the user), or receive a manual input from the user to dispense the appropriate consumable. The base 3804 may also include a monitoring system 3824 configured to track distribution of consumables units from the one or more containers, such as by tracking when a consumable unit is dispensed or detecting a retrieval of one of the consumable units that has been dispensed by the base 3804 or one of the containers 3802. This may include any suitable device or systems including a camera, touch sensors, beam-breaking detection, a pressure or weight sensor, and so forth.

The base 3804 may generate a notification under a variety of conditions and transmit the notification through a variety of channels. For example, the base 3804 may provide a notification that a consumable unit has been dispensed from the base 3804, which may be sent to a remote healthcare system or any other suitable recipient. The notification may also or instead include a notification (e.g., to a healthcare system) when a consumable unit is retrieved after dispensing. A notification may also or instead be generated to alert the user of a dosage in the schedule 3818. In another aspect, the notification may include a compliance report concerning the schedule 3818, which may be communicated to one or more third parties such as a healthcare provider or any other user-designated contact.

The notification may be based on a tiered notification scheme. For example, a first notification may be an alert to the user when a dosage is due. A second notification may be an alert to the user when the dosage is missed within or after a predetermined time interval of a scheduled time for the dosage. A third notification may be an alert to the user when the user does not respond to the prior alert within a predetermined time. The third notification may also include a notification to any suitable notification processing system, which may reside for example in the remote resource 3808, to contact the user. The notification processing system may include a call center, an automated triage system, an automated message routing system, an instant messaging center, a customer service center, or any other system for automated or human response. In another aspect, the third notification may be transmitted to a health care professional or to a predetermined contact for the user. More generally, the systems described herein may be configured to use notification states that escalate based on trigger events, such as by providing a sequence of escalating notifications using a number of different communication mediums according to deviations from the schedule 3818.

The base 3804 may provide a notification through any suitable notification hardware 3850 for local notification such as a buzzer, a speaker, a display, a projector, or a light-emitting diode. The projector may be a video projector or laser system that can project a written or graphic notification on nearby surfaces. In another aspect, the notification may include a text message, an electronic mail, a telephone message, or any other form of message or communication, which may be generated directly by the base 3804 or generated indirectly through the remote resource 3808 in response to the schedule 3818 or a signal from the base 3804.

In a general sense, the base 3804 may transmit any user-configured notification to any user-selected entity at any time, such as when a consumable unit is dispensed or retrieved. In one aspect, the base 3804 may include a notification system that is remotely configurable by a third party to provide one or more notifications according to deviations from the schedule 3818.

While a single base 3804 is depicted in the figure, it will be understood that the system 3800 may include any number of bases, each storing a schedule. These bases and schedules may be for a single user, or for a number of different users, with the association between particular users and bases being flexibly configurable as described herein. As described herein, a server for managing bases may be provided as a remote resource, or hosted on one of the bases, or some combination of these.

The network interface 3806 may be any suitable interface for coupling the base 3804 in a communicating relationship with the data network 3810 and various devices coupled thereto. In one aspect, communications between the base 3804 and the remote resource 3808 may use 256 bit encryption or any other strength or type of security mandated by regulation or health care best practices.

The remote resource 3808 may be any remote computing facility or combination of facilities including cloud computing resources, databases, remote applications, and so forth. The remote resource 3808 may for example, be a resource provided by a participant in a healthcare system such as a health care provider system, a health insurance provider system, a retailer, a pharmacy, a patient group, a consumer group, or any other group or organization. The base 3804 may provide the schedule 3818, or information about the schedule, to the remote resource 3808, which may be configured to provide a notification based on the schedule 3818. This may, for example, be a notification that a scheduled item has been missed, that a scheduled item is upcoming, that a scheduled item has been completed, and so forth.

In one aspect, the remote resource 3808 may include a server with a memory storing a number of schedules for dispensing consumables or other dispensables to a number of users. The server may provide an interface such as a web-based user interface for updating one of the schedules, such as any of the management interfaces described herein.

In one aspect, the remote resource 3808 may host an order fulfillment system that compares a numeric count of the consumable units in the containers 3802 to the schedule 3818 to determine when replacement consumables should be ordered for a user. For example, the base 3804 may periodically inventory contents of the containers 3802 and provide relevant information concerning current counts, remaining time with current inventory, and the like to the remote resource 3808. It will be appreciated that the order fulfillment system may also or instead be hosted on the processor 3812 of the base 3804, or distributed or shared in any other suitable manner. The order fulfillment system may be configured to automatically place an order for a replacement container, or an order for replacement consumables in bulk form that can be used to refill one of the containers. Similarly, the order fulfillment system may be configured to notify the user to order a replacement container or replacement consumables in bulk form.

In another aspect, the remote resource 3808 may include a remote management system. The remote management system may generally be operable to manage consumables at the base 3804 in a manner consistent with expected uses according to the schedule 3818. Thus for example, the remote management system may identify a predetermined level in one of the containers 3803, which may be any level suitable for action. The predetermined level may be specified as a state such as full, low, empty and so forth, or as a percentage full, a number of doses remaining, or in any other suitable manner.

When the predetermined level has been determined, the remote management system may take appropriate next steps such as determining whether a prescription for the user includes additional dosages for a type of medication in the one of the one or more containers, e.g., by retrieving prescription information for the user from another remote resource or from the memory 3816 of the base 3804. With this information, the remote management system may provide a prescription verification based upon which the remote management system can initiate a variety of additional steps. For example, the remote management system may initiate a managed care billing request for a replacement container, a payment from the user for the replacement container, or placement of an order for the replacement container with a vendor. The remote management system may similarly initiate a billing request, payment, or order for a bulk consumable to refill one of the containers 3802.

In another aspect, the remote management system may provide a variety of other prescription-related or compliance-related functions. For example, the remote management system may monitor compliance for the user according to one or more prescriptions from one or more health care providers, which may be included from the schedule 3818 or retrieved from the health care providers. As another example, the remote management system may compare various prescriptions from health care providers to ensure compatibility of the one or more prescriptions for a particular user. The remote management system may also or instead compare consumable units in the schedule for drug interactions based on data from one or more of warning databases, government sources, drug label information, pharmaceutical companies, healthcare groups, health care providers, and patient groups. In another aspect, the remote management system may monitor consumable units dispensed from all of the containers registered with the base to the user to determine an actual medication regime for the user, and to check counter-indications within the actual medication regime. The remote management system may be configured to generate an alert to a healthcare provider or some other predetermined contact for a counter-indication identified within the schedule 3818. This approach to counter-indications advantageously ensures that all medications are accounted for by centralizing tracking at a single location.

The remote management system, aspects of which may also be realized as a management system on the base, may be configured to manage the schedule 3818. The management system may also control the security lock 3840 to prevent dispensation of a consumable unit prior to a corresponding dosage in the schedule 3818. In another aspect, the management system may track an expiration date for the consumable units in the containers 3802, and control the security lock to prevent dispensation of consumables after they have expired. Where the consumable units include medicine such as a prescription medicine or an over-the-counter medicine, the management system may control the security lock 3840 specifically to prevent overdosing with such medicine.

Similarly, the remote resource 3808 may provide a server for various other functions within the system 3800. For example, the base 3804 may be configured to receive an update to the schedule 3818 from the server, thus permitting cloud-based management of the schedule 3818 to provide a location-independent scheduling resource. In another aspect, the remote resource 3808 may provide a server configured to controllably associate the base 3804 (or a number of bases) with a user to provide an associated base. More generally, the base 3804 may be associated with any number of users and any number of bases may be associated with a particular user. These mappings may be stored by and managed through the server, e.g., using the various interfaces described herein.

When the base 3804 becomes an "associated base" that is associated with a user, the base 3804 may respond to the association in numerous ways consistent with operating the associated base for the user. For example, the associated base may retrieve a schedule for the user, or evaluate contents of dispensers physically associated with the base for availability of consumables indicated in a schedule for the user. The associated base may then more generally operate as contemplated herein, such as by generating a notification to a user when a consumable in an associated dispenser is at a predetermined level (such as low or empty), automatically dispensing a consumable in response to the schedule 3818, or monitoring compliance of the user with the schedule 3818. The base 3804 may also notify the server or relevant events such as a change in configuration of dispensers or containers physically associated with the base 3804 (e.g., insertion or removal of a dispenser) and the server may perform management functions such as requesting a change in configuration of the dispensers, e.g., according to the schedule 3818.

In another aspect, the remote resource 3808 may include a financial processing system to support payment processing for various actions related to the schedule 3818 or the user. For example, the financial processing system may be configured to initiate a payment authorization from the user for a replacement container, a payment authorization from a health insurance provider for the replacement container, or a payment authorization from a third party payor other than a health insurer for the replacement container.

In another aspect, the remote resource 3808 may include a goal setting platform configured to receive a goal of a user and provide reminders to the user related to the consumable units in the containers 3802. The notification may include a reminder related to the goal and unrelated to the consumables, or a reminder related to the goal and related to the consumables, or any other suitable reminder. The goal setting platform may also usefully be hosted on the processor 3812 of the base station 3804 for local execution.

The data network 3810 may include any network(s) or internetwork(s) suitable for communicating data and control information among participants in the system 3800. This may include public networks such as the Internet, private networks, telecommunications networks such as the Public Switched Telephone Network or cellular networks using third generation (e.g., 3G or IMT-2000), fourth generation (e.g., LTE (E-UTRA) or WiMax-Advanced (IEEE 802.16m), as well as any of a variety of corporate area or local area networks and other switches, routers, hubs, gateways, and the like that might be used to carry data among participants in the system 3800. Components linked through the data network 3810 may be linked through a public network such as the Internet, or through a local area network or other local communication link.

The slots 3814 may include any electromechanical interface for removably and replaceably receiving containers 3802. The slots 3814 may include active components that communicate with a security lock 3840 to control removal and replacement of containers 3802, or to control dispensation of consumable units from the containers 3802. Where the containers 3802 include sensors, memory, processing, and the like, the slots 3814 may also include an electrical interface for coupling the containers 3802 in a communicating relationship with the base 3804. In this manner, when the containers 3802 are placed into the slots 3814, the containers 3802 may provide status information to, or receive programming and data such as scheduling information from, the base

3804. While the base 3804 is generally described as a multi-container device, it will be understood that the various features and functions of the base 3804 as described herein may usefully be incorporated into a single dispenser of consumables. As such, the base 3804 may be a dispenser housing a single container and including a user input to dispense the consumable units from the single container in unit form. This may be any of the cartridges or other dispenser described above, or any other suitable unit dispenser of consumables or other dispensables. Similarly, the container 3802 described herein may include a dispenser configured to dispense individual ones of the plurality of consumable units independently from the base 3804, that is without being couple to or controlled by the base 3804.

The schedule 3818 may be any schedule useful for operating the base 3804 or the containers 3802, or for coordinating operation of the foregoing with requirements of a user or a third party such as a health care professional. For example, the schedule 3818 may be a user-created dosing schedule. The first remote device 3820 may automatically generate a change to the schedule 3818 using any appropriate rules, algorithms, or other constraints. For example, the first remote device 3820 may provide counter-indication screening. In response to an update to counter-indication data provided by a pharmaceutical company, health care provider, government agency or the like, the first remote device 3820 may automatically screen for counter-indications in the schedule 3818 and mitigate conflicts as appropriate. As another example, the first remote device 3820 may receiving data from the base 3804 concerning actual dosing distributed from the containers 3802 and update the schedule 3818 accordingly. More generally, a variety of automated updates may be supported using any events that can be detected by the first remote device 3820 including event identified by a health care provider, events detected at a locale of the base 3804, events detected by other online resources, and so forth.

The second remote device 3822 may in general be any remote device coupled to and participating in a dispensable management system such as the system 3800 described herein. In one aspect, the second remote device 3822 may be a mobile device such as a smart phone or wearable computing device associated with the user and configured to receive the notification. In another aspect, the second remote device 3822 may be a wearable accessory such as a bracelet, pendant, or earpiece associated with the user and configured to receive the notification. In either case, the device 3822 may receive a notification remotely through the data network 3810 or locally, such as through a local area network or direct short range communication with the base 3804. A wearable accessory may be associated with the user or with the base 3804, and may usefully provide a two-way communication system for the user to provide information to the base 3804, and for the user to receive notifications from the base 3804, e.g., about the schedule 3818, contents of the containers 3802, and so forth.

While described as being stored in a memory of the base 3804, it will be understood that the schedule 3818 may also or instead be hosted at another location such as the remote resource 3808, which may in this case be another computer owned by the user, a schedule management system, a data repository, another base associated with the user, a healthcare provider system, and so forth.

In one aspect, the first remote device 3820 and the second remote device 3822 may be accessories for use by users in managing and using the schedule 3818. For example, the first accessory may be couple in a communicating relationship with a server (e.g., a server hosted on the base 3804 or on the remote resource 3808) and configured to provide a notification to a user based on a schedule associated with the user, such as the schedule 3818. This accessory may be a wearable accessory such as a bracelet, pendant, watch, or the like, and may be configured to receive an input from a wearer to dispense a consumable from one of the containers 3802. The first accessory may include a sensor 3821 such as a biometric sensor configured to capture biometric data of a wearer. This may include information used for biometric identification or authorization, or this may include health and fitness information such as a heart rate, blood pressure, or any other useful information that might be obtained from a wearer using sensors on the accessory. In another aspect, the sensor 3821 may include a location sensor (e.g., GPS, proximity sensor, WiFi positional sensor, or the like) configured to determine a location of the wearer. Information obtained from the sensor 3821 may be transmitted from the accessory to any suitable location, such as the base 3804, the remote resource 3808, or any other server or other data repository or the like. The first accessory may be associated with numerous users, and may include detection circuitry to determine which one of a number of users is wearing or operating the accessory.

The second remote device 3822 may be a second accessory similarly coupled to the system 3800 and configured to communicate a notification from the second accessory to the first accessory. In this manner, a third party such as a friend, family member, or health care provider may signal a user through the interconnected accessories to consume one of the consumables in one of the containers 3802 at any desired interval, either as a reminder from a preexisting schedule or as an ad hoc dosage indication. In another aspect, the second accessory may be associated with the user. It will be understood that both accessories may be intended for use by the user, or one of the accessories may be associated with the user and intended for use by a third party. In this manner, the third party may use the second accessory for any suitable notifications to the user. Similarly, the second accessory may associated with a number of different users to facilitate, e.g., group notification or management of group schedules.

In one aspect, the base 3804, the remote resource 3808, or some combination of these may be configured as a messaging system to support communications and synchronization among various bases, containers, dispensers, accessories and other devices associated with a user.

The system may include a management interface 3830 including a graphical interface for managing the schedule 3818 and related elements of the system 3800. The management interface 3830 may be hosted on the remote resource 3808, the base 3804, or some other location, or combinations of these. The management interface 3830 may be deployed as a web interface or the like served by a web server hosted on the base 3830, or on the remote resource 3808, and remotely accessible through the data network 3810. In one aspect, the base 3804 may include a display 3832 for local access to the management interface 3830 directly from the base 3804. The management interface 3830 may be configured for various administrative functions. For example, the management interface 3830 may be configured for a user to modify the schedule 3818. The management interface 3830 may also or instead be configured to limit modifications to the schedule to authenticated individuals, qualified healthcare professionals (which may be authenticated), or an electronic healthcare information technology system, or any combination of these or other users or systems. In another aspect, the management interface 3830 may be configured to display compliance information, e.g., to any of the foregoing users.

In another aspect, the management interface may provide an interface for modifying an association of a user with the base 3804. In general, a base 3804 may have any number of users associated with it, with the schedule of each user maintained in the memory 3816 of the base 3804 or any other suitable location, such as the remote resource 3808. This association may be controlled to add or remove users for the base 3804, or to add or remove associations of a particular user with a number of bases. In either case, these associations may be used to update schedules so that a particular base has suitable scheduling information for any and all associated users, and similarly so that a particular user has appropriate scheduling information on any and all associated bases.

The system 3800 may include a security lock 3840. In general, this may be a physical locking mechanism such as any of the locking mechanisms described herein to physically retain containers 3802 in the slots 3814 or to providing authenticated access to containers 3802 or contents thereof. This may also or instead include a virtual locking mechanism configured to secure data on the base 3804 or access to the data in the containers 3802. For example, the remote resource 3808 may be configured to remotely lock the base 3804 to prevent dispensation of consumable units from one or more of the containers 3802 using the security lock 3840.

While depicted on the base 3804, it will be understood that the security lock 3840 may also or instead be on an individual container 3802, or on the remote resource 3808, or distributed in any suitable manner among these system components. In one aspect, the security lock 3840 may require authentication of a user as a condition for dispensation of one of the consumable units from one of the containers 3802. The security lock 3840 may include any of a variety of inputs. For example, the security lock 3840 may include a user input on the base 3804 operable to unlock one of the containers 3802 in response to a user input when the container 3802 is coupled to the base 3804. In another aspect, the security lock 3840 may include a user input on the container 3802 (which may be a simple container or a cartridge as described above) to unlock the container 3802 in response to a user input.

Regardless of location, the security lock 3840 may include a variety of interfaces. For example, the security lock 3840 may include a keypad configured for passcode authentication of the user. The security lock 3840 may also or instead include a biometric system for authenticating the user such as a voice recognition user interface for voice authentication, a facial recognition system, a fingerprint identification system, an iris scanner, or the like.

The security lock 3840 may authenticate the user with reference to the remote resource 3808, which may provide information about the user or operate as a trusted certificate authority or the like. In one aspect, the remote resource 3808 may include a data repository for electronic medical records that can be used in authenticating the user. The security lock 3840 may be controlled remotely, e.g., through the data network 3810, to provide a remote controlled security lock for remotely controlling access to the consumable units in the containers 3802. Where the monitoring system 3824 includes a camera, the security lock 3840 may be configured to respond to an access attempt by capturing an image with the camera. The camera may be a digital still camera or a video camera directed toward a location of an operator of an interface of the security lock, such as an area in front of a keypad, where an image may be captured to document access attempts. The image or images captured from this camera may be processed using facial recognition software and a local or remote database for face recognition. This may be useful in detecting tampering or other improper uses, particularly in identifying an operator where an authentication fails. Further actuations and processing may be triggered by successful or unsuccessful authentication and security unlocking, including but not limited to audio alarms, visual alarms, physical device movements, physical lockdowns, and electrical jolts or shocks.

The security lock 3840 may provide additional locking, security, or authentication related functions. For example, where the container 3802 is a dispenser with a user input for manual activation of a dispensing mechanism, the security lock 3840 may control activation of the user input. Where the container 3802 is a dispenser with a machine input for remote machine activation of a dispensing mechanism (e.g., from a base to which the container 3802 is coupled), then the security lock 3840 may control activation of the machine input. The security lock 3840 may also or instead require authentication of a user as a condition for removing one of the containers 3802 from the base.

A container, dispenser, and/or base may perform self-diagnostics, including but not limited to checking cleanliness and residue, checking digital memory faults, checking onboard data against redundant data sources both local and remote, power supply tests, and battery tests. The device may perform such diagnostics either as an individual, or by utilizing other local and remote devices and resources that are connected to it. The device may also perform such diagnostics upon user, environmental, or self-created triggers. Thus the device and any other system devices previously described in previous paragraphs may form a self-regulating, self-testing, and self-reliant dispensables system that may require no manual or user input to drive its diagnostic functionality.

Furthermore, such self-reliance of this dispensables system may translate beyond diagnostic functionality to the full set of functionality described in this document. An illustrative example is a dispensing device described herein, which provides doses of consumables to a user automatically based on an environmental trigger, such as development of an illness, instead of manually.

Figure 39:
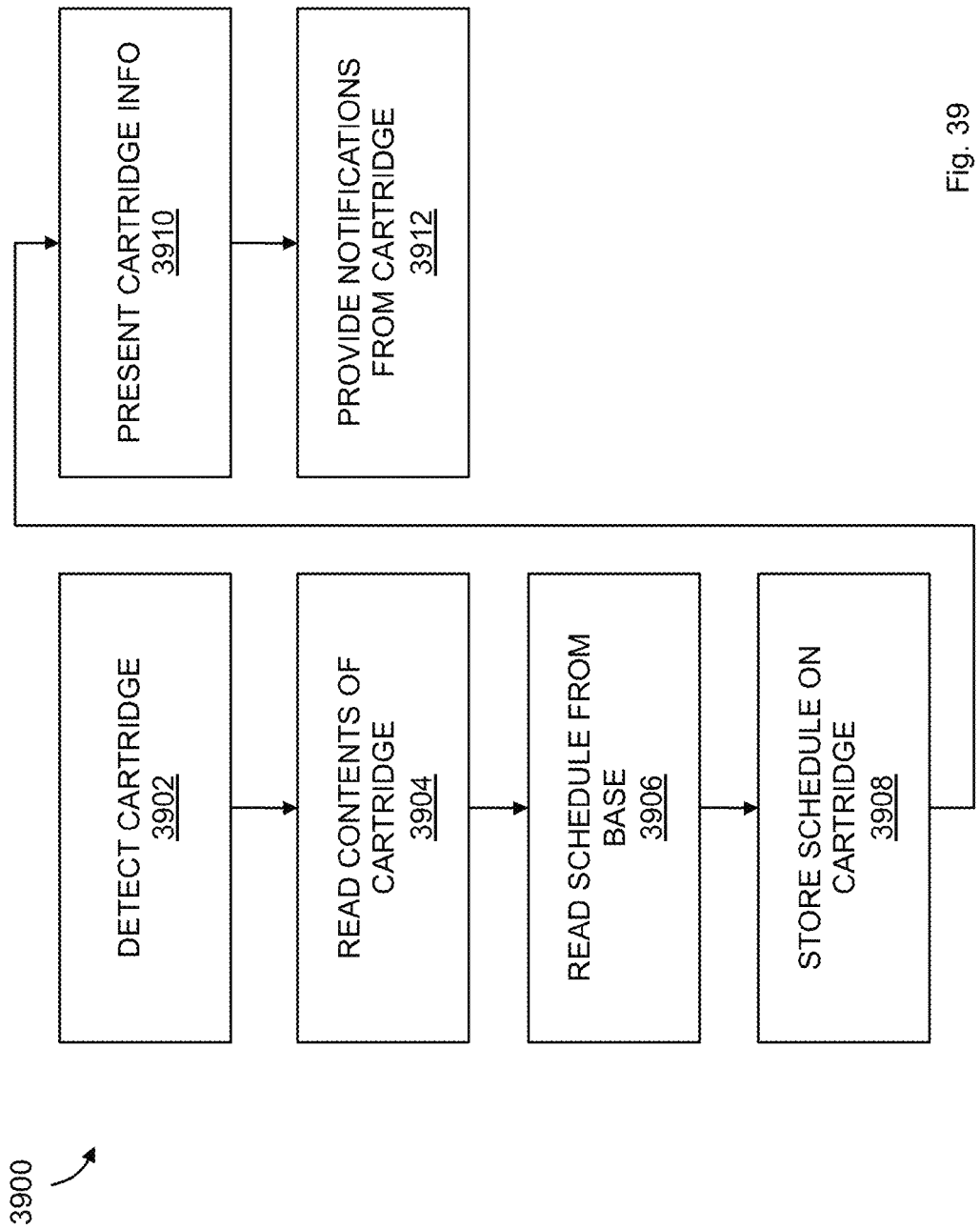
FIG. 39 shows a method for synchronizing scheduling data and dispensables data among various devices.

FIG. 39 shows a method for synchronizing scheduling data and dispensables data among various devices. In general, the method 3900 may be used to synchronize data during periodic removals and replacements of cartridges, containers and the like into bases.

As shown in step 3902, the method 3900 may begin with detecting an insertion of a cartridge containing consumables into a base. This may, for example, be any of the cartridges, consumables, and bases described herein. The cartridge, for example, may include an integrated dispensing cartridge, or a container for consumables with a removable and replaceable housing for the container that provides an electro-mechanical interface configured to removably and replaceably couple to the base, such as any of the clip/cartridge combinations described above. In another aspect, this cartridge referred to herein may be a simple container of consumables or other dispensables that can be inserted into the base. The insertion may be detected, e.g., through electrical contact with two or more exposed conductive surfaces, activation of a mechanical switch, plunger, or the like, or through other means such as optical detection using a camera or an optical beam and sensor. However detected, the detection may cause a processor on the base or other processing circuitry to initiate a number of steps to incorporate the inserted cartridge into the resources of the base.

As shown in step 3904, the method 3900 may include reading the contents of the detected cartridge. This may for example, include reading a numeric amount of the consumables from the cartridge and communicating the numeric amount to the base. This may for example including reading data from a memory in the cartridge or directly from a memory in a clip that holds the cartridge, or using sensors or the like to detect a current numeric amount in a reservoir of the cartridge. While numeric count is one useful property of cartridge contents, this may also or instead include reading any other information about the cartridge such as a type of contents, a percentage fullness, a cartridge identifier, an expiration date of contents, and so forth. In general, such information may be directly encoded in a memory of the cartridge for access by the base, or amenable to detection through sensors or the like on the cartridge, an associated clip, or the base itself.

However determined, this information may then be communicated to the base using any suitable communications interface. While the insertion of the cartridge into the base makes wired contacts and corresponding wired communications convenient, it will be understood that this communication may also or instead including wireless communication using WiFi, near field communications, radio frequency identification tag technology, or any other non-contact communication techniques.

As shown in step 3906, the method 3900 may include reading information from the base for communication to the cartridge. For example, this may include reading a schedule for medication or other dispensables from the base (e.g., from a memory of the base) and communicating a portion of the schedule relating to the consumables in the cartridge to the cartridge. It will be understood that the entire schedule may also be sent to the cartridge, such as for porting the schedule to another location. However, the portion relating to the consumables permits the cartridge to operate independently as a dispenser for the consumables according to the schedule, and the base, which contains or has access to broader, more integrated information about a dispensables plan for a user may usefully update the schedule on the cartridge as the overall schedule changes. This information may be communicated to the cartridge using any suitable communications interface.

After this exchange of information—numeric count to base and schedule to cartridge—a variety of other functions may usefully be performed.

As shown in step 3908, the method 3900 may include storing the schedule and the numeric amount of consumables, along with any other information, in a memory independent from the base for independent operation of the cartridge when uncoupled from the base. In one aspect, this may include a memory of the cartridge. In another aspect, this may include a remotely accessible memory store that the cartridge can access, e.g., through a wireless or cellular network, or when connected to other bases not associated with the user.

As shown in step 3910, the method 3900 may include presenting cartridge information such as a numeric count to a user. This may, for example, include providing an audio output including the numeric count in spoken form or displaying the numeric amount on a display of the cartridge or the base. Thus, when a cartridge is connected, the cartridge may display the numeric account, and the base may issue an audible notification in spoken form, such as "this cartridge contains five units." Where the dispensable type is also available, either directly from the cartridge or based on an identifier for the cartridge, this may be a more complete statement of the status of the cartridge such as "this cartridge contains five units of aspirin which will expire on Jan. 3, 2015."

As shown in step 3912, the method 3900 may include issuing a notification from the cartridge based upon the predetermined schedule. This may include any useful notification including local notifications such as a display, a sound, or a vibration from the cartridge itself, or a notification to the user through some other communication medium such as instant messaging, electronic mail, or the like.

Figure 40:
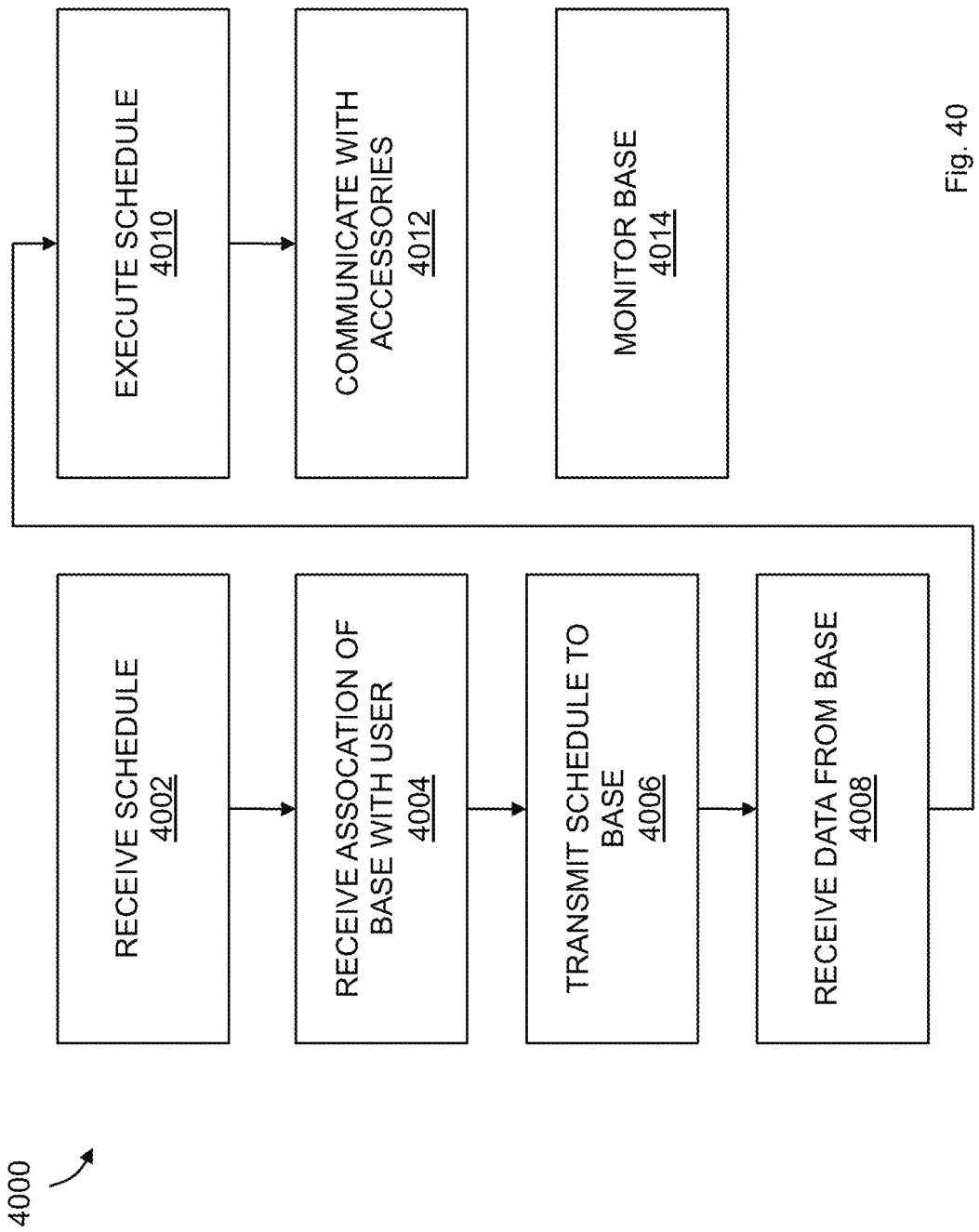
FIG. 40 shows a method for managing user associations with system components.

FIG. 40 shows a method for managing user associations with system components. In general, the method 4000 may include a variety of synchronization and coordination steps managed, e.g., by a server hosted on a base or a remote resource.

As shown in step 4002, the method 4000 may begin with receiving a schedule for dispensing consumables to a user. In one aspect, a user may provide the file as a schedule file, or create the schedule in a user interface. In another aspect, the schedule may be received from a base or other device. For example, this may include a communication manually initiated by a user, or an automatic communication that is periodically transmitted to update the schedule, or initiated in response to an event such as when a base joins the system, becomes associated with a user, receives a schedule change, or the like. In general, this may also include receiving a user-generated update to the schedule to create an updated schedule that can be transmitted to the base for execution as generally described below.

As shown in step 4004, the method 4000 may include receiving an association of a base with the user, such as through an input to a management interface or the like as described herein.

As shown in step 4006, the method 4000 may include transmitting the schedule to the base. Thus, when an association is detected, the associated base can be configured to execute a schedule for the associated user. As generally described herein, the base may be operable to execute the schedule by providing notifications to the user and by dispensing unit form dispensables such as consumables from containers that are removable from and replaceable to the base. As used in this context, it will be understood that the containers may be simple containers, cartridges, and/or cartridge/clip combinations as described herein.

As shown in step 4008, the method 400 may include receiving data from the base characterizing a type and quantity of consumables in each of the containers, along with any other information that might be usefully provided from the containers and/or base.

As shown in step 4010, the method 4000 may include executing the schedule from the base. As described herein, this may include providing local notifications, communicating notifications to other devices, automatically or manually dispensing items, monitoring compliance, and so forth.

As shown in step 4012, the method 4000 may include communicating with accessories such as a mobile device (e.g., smart phone, tablet) or a wearable accessory associated with the user. In one aspect, this may include transmitting a notification from the schedule to any device such as a mobile device or wearable accessory associated with the user. Similarly, this may include receiving an instruction from the mobile device or wearable accessory, such as an instruction to dispense a consumable from one of the containers coupled to the base.

As shown in step 4014, the method 4000 may include monitoring the base, along with the contents of containers associated with the base. For example, this may include determining when one of the containers needs to be replaced or refilled base on the schedule, along with data received from the base characterizing the type and quantity of consumables in the containers, and then generating a notification to the user to replace the corresponding container(s). Similarly, this may include automatically ordering a replacement for one of the containers, or for bulk consumables to refill the container.

Automatic ordering may include any suitable, computer-coordinated interactions with appropriate approval, fulfillment, and payment platforms such as those described herein. This may also include determining when the base needs to be reconfigured, e.g., with the addition, removal, replacement, or refilling of containers. Fulfillment may include but is not limited to human-driven and drone delivery methods.

According to the foregoing, a method disclosed herein includes detecting an insertion of a cartridge containing consumable units into a base; reading a numeric amount of the consumable units from the cartridge and communicating the numeric amount to the base; and reading a predetermined schedule for medication from the base and communicating a portion of the predetermined schedule relating to the consumable units in the cartridge to the cartridge.

It will be appreciated that the methods and systems described above may serve as a platform for a wide array of enhancements and related features, any of which may be usefully combined with the above. A number of examples are provided below by way of non-limiting example. In one aspect, there is disclosed herein a connection mechanism between a consumable container and a socket on a base station, that (a) has a lock-and-key to securely attach container to the socket and (b) stores digital information about container properties on container in an encrypted/unencrypted data format, that is read by the socket uniquely to prevent misdosing and miscommunication of container properties.

In another aspect, any of the foregoing may include pharmaceutical packaging or filling line that can (a) set cartridge's collar to accommodate pill's specific size (b) attach cartridge data storage device (e.g. NFC sticker). In another aspect, a base may support user-specific authorization or authentication with respect to SKUs and devices within various containers or cartridges of a base, with access established by an account owner or an administrator. The management system may provide a drag-and-drop interface to allocate doses, permissions, regimens, schedules and settings from one user, account or device to another. The interface may be deployed on a base, from a web server, from a user computer, from a mobile device, or from any other suitable hosting site.

In another aspect, the devices herein may use weight-based determination of consumable volume or count in consumable container. In another aspect, the devices herein may include a pill maker for compression of pills to manufacture pills from raw materials, as well as any other suitable mixing, compounding, encapsulating, or other similar functions.

In another aspect, a system described herein supports scheduling consumable use via queuing doses to be consumed on a per-user level, and allowing (a) access/modification to queues for specified 3rd parties, (b) categorization, sorting and filtering by consumable properties including indication, and (c) analytics. In another aspect, a system described herein may be configured for purchasing based on some or all of another user's historical purchase basket ("grabbing"), if that user has shared their purchase history for "grabbing" purposes. In another aspect, the system described herein may be configured to support remote access to dispensing and authorization functions of an electronic consumable dispenser. In another aspect, the systems described herein may be configured to support remote authorization of consumable dispenser usage, particularly in pill compression, by 3rd parties, including but not limited to healthcare providers, officials and regulators.

In another aspect, the systems described herein may be used to provide a variety of notifications such as triggering consumable use alerts based on (a) dose queuing (b) dosing requirements, such as need to take drug with food (c) consumable misuse such as missed dose or overdose (d) unsafe drug interactions (e.g. Drug A and Drug B cause stomach bleeding if consumed within 24 hrs of each other). In another aspect, the systems described herein may be configured to support automatic reordering of consumable SKUs triggered by received data on SKU unit depletion or near-depletion triggered by system data. In another aspect, systems disclosed herein may be configured to support prioritized communications in which online servers and in-home devices use prioritized buffering and transmission to make sure key non-redundant data is transmitted first during any communication.

In another aspect, a central repository may be provided for checking of pharmaceutical products against user data and healthcare information. In another aspect, the system may provide a universal consumable tracking system that (a) resolves between multiple consumable use devices (b) directly interfaces consumption of consumables to personal health records and any other 3rd party health record systems. In another aspect, the system may provide a use processing engine and frontend that enables (a) game-ification of consumable usage (b) automatic and manual consumable goal setting and recognition.

The methods or processes described above, and steps thereof, may be realized in hardware, software, or any combination of these suitable for a particular application. The hardware may include a general-purpose computer and/or dedicated computing device. The processes may be realized in one or more microprocessors, microcontrollers, embedded microcontrollers, programmable digital signal processors, or other programmable device, along with internal and/or external memory. The processes may also, or instead, be embodied in an application specific integrated circuit, a programmable gate array, programmable array logic, or any other device or combination of devices that may be configured to process electronic signals. It will further be appreciated that one or more of the processes may be realized as computer executable code created using a structured programming language such as C, an object oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software.

Thus, in one aspect, each method or step described above and combinations thereof may be realized as a computer program product comprising computer executable code embodied in a computer readable medium (such as a non-transitory computer readable medium) that, when executing on one or more computing devices, performs the steps thereof. In another aspect, the methods may be embodied in systems that perform the steps thereof, and may be distributed across devices in a number of ways, or all of the functionality may be integrated into a dedicated, standalone device or other hardware. In another aspect, means for performing the steps associated with the processes described above may include any of the hardware and/or software described above. All such permutations and combinations are intended to fall within the scope of the present disclosure.

It should further be appreciated that the methods above are provided by way of example. Absent an explicit indication to the contrary, the disclosed steps may be modified, supplemented, omitted, and/or re-ordered without departing from the scope of this disclosure.

The method steps of the disclosures(s) described herein are intended to include any suitable method of causing such method steps to be performed, consistent with the patentability of the following claims, unless a different meaning is expressly provided or otherwise clear from the context. So for example performing the step of X includes any suitable method for causing another party such as a remote user or a remote processing resource (e.g., a server or cloud computer) to perform the step of X. Similarly, performing steps X, Y and Z may include any method of directing or controlling any combination of such other individuals or resources to perform steps X, Y and Z to obtain the benefit of such steps.

While particular embodiments of the present disclosure have been shown and described, it will be apparent to those skilled in the art that various changes and modifications in form and details may be made therein without departing from the spirit and scope of this disclosure and are intended to form a part of the inventive concepts described herein.

What is claimed is:

1. A device comprising:
   a first mechanical interface configured to removably and replaceably couple to a container of consumables;
   a first communication interface configured to receive data from the container relating to a number of consumables in the container when the device is coupled to the container through the first mechanical interface;
   a second mechanical interface configured to removably and replaceably couple to a base;
   a second communication interface configured to receive a schedule for dispensing the consumables from the base when the device is coupled to the base through the second mechanical interface;
   a memory storing the number of consumables and the schedule; and
   a user input actuatable by a user to dispense one of the consumables from the container.

2. The device of claim 1 further comprising a machine input configured to receive a signal from the base when coupled to the base, and to responsively control the container to dispense one of the consumables.

3. The device of claim 1 further comprising a locking mechanism to securely retain the device in a predetermined alignment in the base.

4. The device of claim 1 further comprising a processor.

5. The device of claim 1 further comprising a display configured to display the number of consumables in the container.

6. The device of claim 1 further comprising an output device to notify the user of a time to take one of the consumables according to the schedule, the output device including one or more of a buzzer, a speaker, and a light-emitting diode.

7. The device of claim 1 further comprising a network communications device configured to notify the user of a time to take one of the consumables according to the schedule, the communications device transmitting a notification using at least one of a text message, an electronic mail, a VoIP message, a push notification to a mobile device application, and a telephone message.

8. The device of claim 1 wherein the container includes one or more sensors to detect the number of consumables and circuitry to communicate the number to the device.

9. The device of claim 1 wherein the container includes one or more sensors configured to detect a dispensation of one of the consumables and circuitry to communicate a notification of the dispensation to the device.

10. The device of claim 1 further comprising one or more sensors configured to detect a dispensation of one of the consumables from the container.

11. The device of claim 1 further comprising a wearable accessory coupled in a communicating relationship with the base and configured to provide a notification to a wearer based upon the schedule.

12. The device of claim 1 further comprising a processor configured to retrieve an update to the schedule from the base in response to coupling the device to the base.

13. The device of claim 1 further comprising a processor configured to provide consumables delivery data to the base when the device is coupled to the base.

14. The device of claim 1 further comprising a processor configured to receive expiration data for the consumables when the device is coupled to the base.

15. A computer program product comprising computer executable code embodied in a non-transitory computer readable medium that, when executing on one or more computing devices, performs the steps of:
   detecting an insertion of a cartridge containing consumables into a base, the cartridge including a container for the consumables and a removable and replaceable housing for the container that provides an electro-mechanical interface configured to removably and replaceably couple to the base;
   reading a numeric amount of the consumables from the cartridge and communicating the numeric amount to the base; and
   reading a schedule for medication from the base and communicating a portion of the schedule relating to the consumables in the cartridge to the cartridge.

16. The computer program product of claim 15 further comprising code that performs the step of displaying the numeric amount on a display of the cartridge.

17. The computer program product of claim 15 further comprising code that performs the step of providing an audio output including the numeric amount in spoken form.

18. The computer program product of claim 15 further code that performs the step of issuing a notification from the cartridge based upon the predetermined schedule, the notification including one or more of a display, a sound, and a vibration.

19. The computer program product of claim 15 further comprising code that performs the step of storing the schedule and the numeric amount in a memory independent from the base for independent operation of the cartridge when uncoupled from the base.

\* \* \* \* \*